(12) United States Patent
Jorgensen et al.

(10) Patent No.: US 6,605,223 B2
(45) Date of Patent: Aug. 12, 2003

(54) BLOOD COMPONENT PREPARATION (BCP) DEVICE AND METHOD OF USE THEREOF

(75) Inventors: Glen Jorgensen, Marlboro, MA (US); Donald E. Barry, Norwood, MA (US)

(73) Assignee: MEDIcept, Inc., Ashland, MA (US)

( * ) Notice: Subject to any disclaimer, the term of this patent is extended or adjusted under 35 U.S.C. 154(b) by 0 days.

(21) Appl. No.: 10/008,605

(22) Filed: Oct. 22, 2001

(65) Prior Publication Data

US 2002/0082153 A1 Jun. 27, 2002

Related U.S. Application Data

(63) Continuation-in-part of application No. 09/885,542, filed on Jun. 20, 2001, now abandoned.
(60) Provisional application No. 60/212,865, filed on Jun. 20, 2000.

(51) Int. Cl.[7] ............... B04B 5/02; B04B 5/04; B04B 9/00; B01D 21/26
(52) U.S. Cl. ............ 210/745; 210/782; 210/806; 210/94; 210/143; 210/232; 210/295; 210/304; 210/324; 210/360.1; 210/380.1; 494/2; 494/21; 494/25; 494/26; 494/36; 494/37; 494/45; 494/84; 604/406; 604/410
(58) Field of Search .................. 210/745, 782, 210/806, 94, 143, 295, 232, 304, 360.1, 324, 380.1; 494/21, 25, 2, 26, 36, 37, 45, 84; 604/406, 408, 410

(56) References Cited

U.S. PATENT DOCUMENTS

| 4,927,545 A | 5/1990 | Roginski ............... 210/745 |
| 5,547,591 A | 8/1996 | Hagihara et al. ............ 210/782 |

FOREIGN PATENT DOCUMENTS

| WO | WO 92/00145 | 1/1992 |
| WO | WO 01/97943 A1 | 12/2001 |

*Primary Examiner*—David A. Reifsnyder
(74) *Attorney, Agent, or Firm*—Edwards & Angell, LLP; George W. Neuner; Lisa Swiszcz Hazzard

(57) ABSTRACT

An automated blood separation method and apparatus is described that allows for the separation of multiple units of blood simultaneously. The method and apparatus reliably and quickly separates blood into its components. An auto-balancing feature within the apparatus automatically preferably compensates for the changing state of imbalance, thereby eliminating the need for additional balancing steps during the separation process. The apparatus has a rotor into which a plurality of cassettes can be inserted. The cassettes have a number of sections for the containment of the whole blood and for the separated blood components, which are contained in disposable bags. The rotor is placed into a centrifuge assembly, and the blood components are then separated and transferred to the bags in the individual sections of the cassettes. Means for including secondary separation devices such as filters is included. The manufacturing information regarding the lot identities used and the conditions under which each unit was processed is also included.

40 Claims, 15 Drawing Sheets

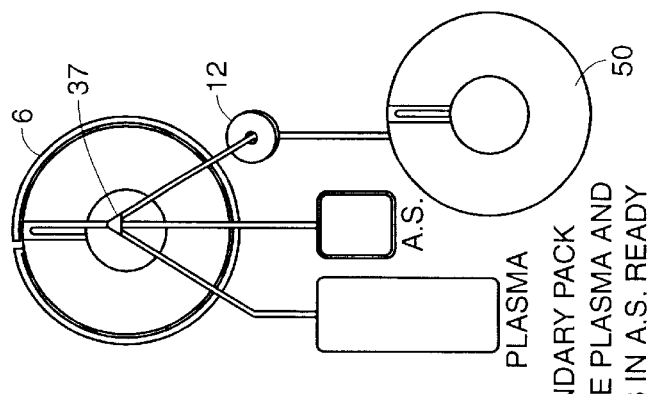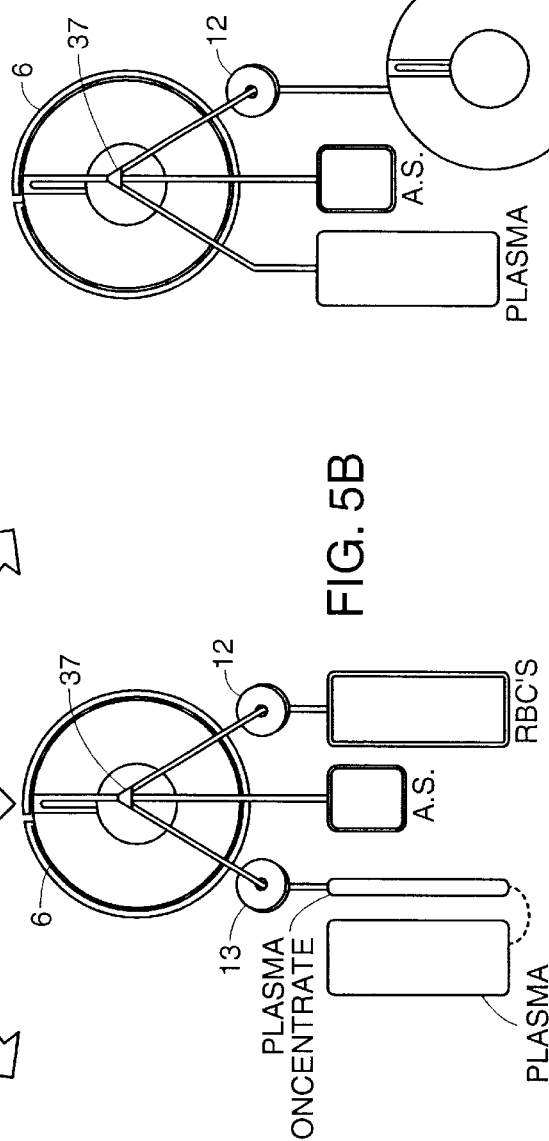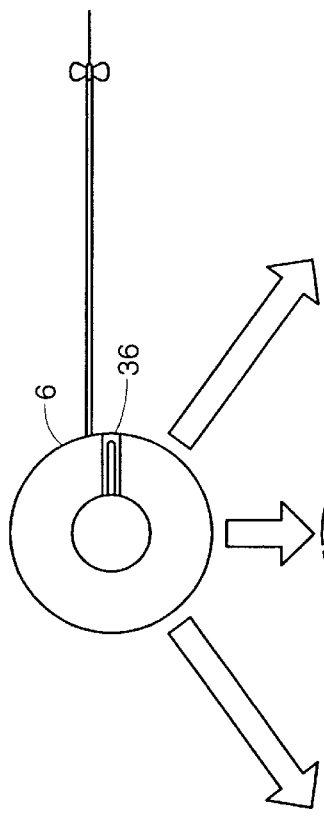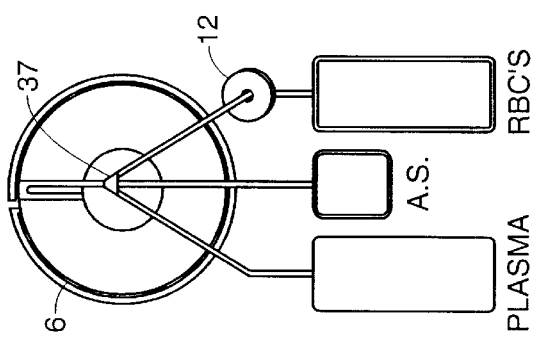
FIG. 5A DOUBLE PACK LUEKODEPLETED RBC'S IN A.S. AND CELL-FREE PLASMA ONLY
FIG. 5B TRIPLE PACK LUEKODEPLETED RBC'S IN A.S. L/D PLT CONCENTRATE, AND CELL-FREE PLASMA
FIG. 5C SECONDARY PACK CELL-FREE PLASMA AND L/D RBC'S IN A.S. READY FOR FURTHER PROCESSING
WHOLE BLOOD COLLECT TRANSFER PACK WITH ACD

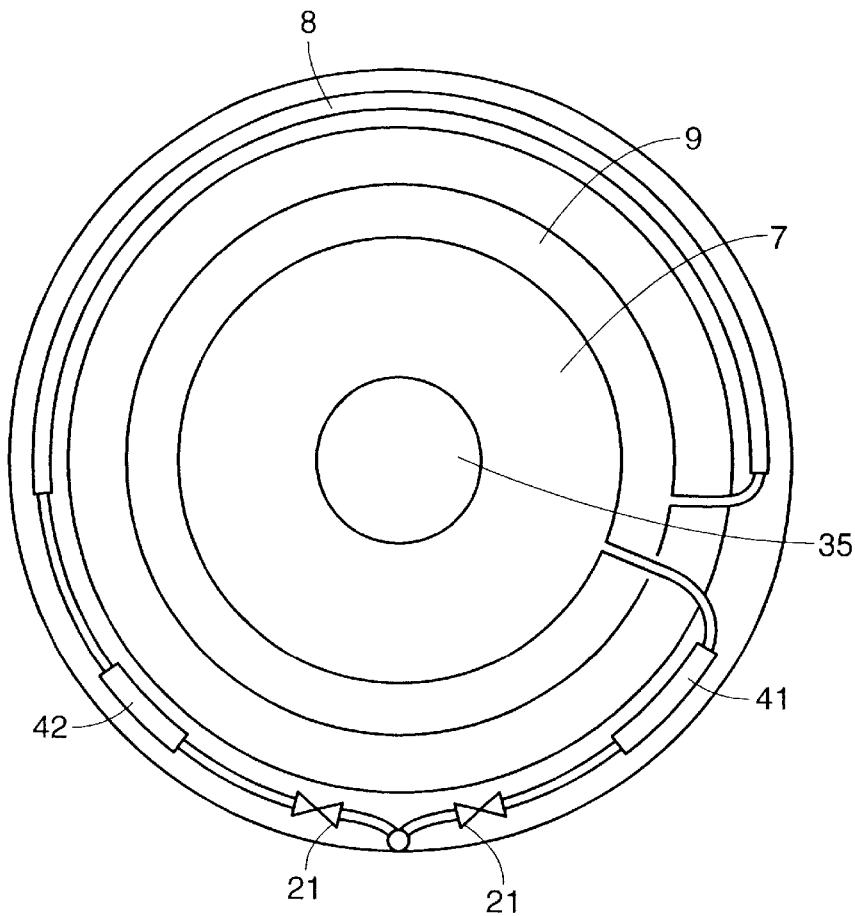
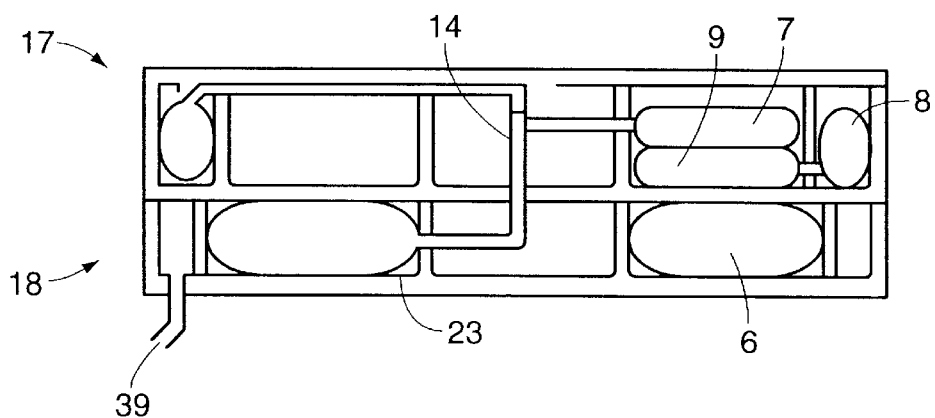
FIG. 10

BLOOD COMPONENT PREPARATION (BCP) DEVICE AND METHOD OF USE THEREOF

The present application claims the benefit of U.S. provisional application No. 60/212,865, filed on Jun. 20, 2000, and a C-I-P of U.S. Pat. No. 09/885,542, filed on Jun. 20, 2001 now abandoned, incorporated herein by reference in their entirety.

FIELD OF THE INVENTION

The present invention relates to methods and apparatus for the separation of one or more cell fractions from their suspending fluid and/or the resuspension of cells in fresh suspending fluid media. More particularly, the invention relates to automated methods and apparatus that allow for the separation of multiple units of blood simultaneously where the red blood cells and platelet cells are separated from the plasma, the red blood cells are subsequently resuspended in a storage solution, and the platelets are suspended in a concentrating volume of plasma. The method and apparatus dramatically decrease the labor and time required to separate blood into its components and simplifies the data retention required to validate the processing parameters for each unit of blood as required by the evolving FDA regulations governing the safety of the nation's blood supply. Other embodiments of the invention include in-line filter elements that remove contaminating cells, called leukocytes, which are believed to be responsible for a variety of adverse reactions by the recipient of the blood components. Similarly, other types of filters and packed columns positioned in-line with the flow of these blood components can remove viruses, bacteria or other contaminants, which further enhances the purity and safety of the blood components.

BACKGROUND OF THE INVENTION

Approximately 12 million units of blood are collected annually in the United States. Another 8 million are collected in the rest of the world. Each donated unit of blood is referred to as "whole blood." Whole blood contains red blood cells, white blood cells and platelets suspended in a proteinaceous fluid called plasma. Because patients often do not require all of the components of whole blood, most units of whole blood are separated into their multiple components. Individual components are then transfused to different individuals with different needs, a practice referred to as "blood component therapy".

Red blood cells carry oxygen and usually are used to treat patients with anemia. For example, patients with chronic anemia resulting from disorders such as kidney failure, malignancies, or gastrointestinal bleeding and those with acute blood loss resulting from trauma or surgery. White blood cells are responsible for protecting the body from invasion by foreign substances such as bacteria, fungi and viruses.

Plasma contains albumin, fibrinogen, globulins and other clotting proteins. Albumin is a chief protein constituent, fibrinogen plays an important role in the clotting of blood and globulins include antibodies. Thus, plasma serves many functions, including maintenance of satisfactory blood pressures and volume, the control of bleeding by blood clotting, immunity and maintenance of a proper balance of vital minerals in the body. Plasma typically is transfused to control bleeding due to low levels of some clotting factors or it may be transfused to expand the volume of circulating blood. Plasma also may be further fractionated to derive its component proteins.

Platelets help the clotting process by sticking to the lining of blood vessels. Platelets are generally used to improve wound healing and stop bleeding, for example, in patients with leukemia and other forms of cancer.

Cryoprecipitated Antihemophilic Factor (AHF) is rich in certain clotting factors, including Factor VIII, fibrinogen, von Willebrand factor and Factor XIII. It is used to prevent or control bleeding in individuals with hemophilia and von Willebrand's disease, which are common, inherited major coagulation abnormalities.

Whole blood will separate into its components if treated to prevent clotting and permitted to stand in a container. The red blood cells, weighing the most, will settle to the bottom, the plasma will stay on top, and the white blood cells and platelets will remain suspended between the plasma and the red blood cells. Typically, a centrifuge process is used to speed up this separation.

A common centrifuge process is described in the AABB Technical Manual, methods 9.4 and 9.11 as follows: Typically, the bag of whole blood is carefully loaded into one of the buckets of a large swinging bucket centrifuge. The opposing buckets are weighed and balanced so that their weight is within a few grams. Then, the buckets are loaded into a rotor and the rotor spun at conditions called "light spin" by the blood banking community (2000 g for 3 min).

After a considerable wait for the centrifuge to slowly decelerate to zero speed, each bucket is very carefully removed from the rotor so that the bags can be removed from the buckets. This delicate operation must be done in a way that does not disturb or in any way re-suspend the cells. The bag is placed between the two expressing plates of a plasma extractor which force the platelet-rich plasma (PRP) from the whole blood bag to the platelet storage bag. A bag of nutrient solution then is emptied into the packaged red cell bag which is, in turn, placed in storage. The platelet-rich plasma (PRP) can be used to prepare platelets and plasma or Cryoprecipitated AHF.

To make platelets, the platelet-rich plasma (PRP) bags again are balanced and then placed back in the centrifuge for a "heavy spin" (5000 g for 5 minutes) causing the platelets to settle at the bottom of the bag. Plasma and platelets then are separated and made available for transfusion. A plasma extractor generally is used to remove all but 50 to 70 ml of plasma, which is required to maintain viability of the platelets. The plasma also may be pooled with plasma from other donors and further processed, or fractionated to provide purified plasma proteins such as albumin, immunoglobulin and clotting factors. Cryoprecipitated AHF may be made from fresh frozen plasma by freezing and then slowly thawing the plasma.

In each case, the components must each be identified in inventory by a method that allows for the traceablilty of that component back to the test results for the original donor, the donated unit, the disposable set in which it was collected, the centrifuge in which it was processed, and, if applicable, the leuko-filter that was used. This traceability is required by law.

Although the centrifuge process speeds up separation of the whole blood into its components, the process is labor intensive and prone to errors and even the most sophisticated inventory control system is subject to the possibility of error as hundreds of data entries are input manually for each unit.

A method and apparatus for the separation of whole blood that is quick, easy and less prone to errors still is needed.

SUMMARY OF THE PRESENT INVENTION

The present invention provides an improved method and apparatus for the separation of whole blood into its components. The method and apparatus automates the separation process, thereby dramatically reducing the labor involved in conventional separation of whole blood. Further, the method and apparatus allows for the separation of multiple units simultaneously, thereby dramatically reducing separation time.

In a preferred embodiment of the present invention, the apparatus includes a centrifuge designed for holding, on a hollow central drive shaft, a plurality of circular cassettes stacked in a co-axial configuration. Each circular cassette has a plurality of cavities for holding a plurality of bags, e.g. a whole blood bag and blood component bags including, for example, a red blood cell bag, a platelet concentrate bag and a platelet poor plasma bag. The cassettes may include further cavities for holding additional components such as filters, other storage bags and an expressor chamber or expressor bag. The various bags are in fluid communication with each other by, for example, tubing or the like to allow transfer of components from one bag to the other. The co-axial configuration is advantageous in that it is self-balancing as the components move from one compartment to another.

Preferably, the whole blood bag and blood component bags are fabricated of materials that allows them to expand and contract repeatedly to move fluids between the cavities. Such materials may include, for example, flexible plastics and elastomeric materials. The number of blood component bags, like the number of cavities, is not limited. The bags for holding the whole blood and blood components are sterile bags fabricated of materials that are of the kind generally approved and accepted for that purpose. Preferably, these bags are shaped to fit the shape of the cassette cavities into which they are placed. Valves and sensors are preferably included in the device to detect and control the flow of the components into the appropriate blood component bag.

In one embodiment, two different types of valves are used. First, an electronic solenoid-driven or motor-driven valve can be used to pinch the tubing connecting the whole blood bag to the red blood cell bag to stop the flow of plasma from being expressed from the whole blood bag as soon as red cells are optically detected in the stream, thereby signaling the end of the expression step. Both the optic detector and the solenoid valve can be controlled by a microprocessor-based logic controller, preferably co-located in the hollow central drive shaft of the device. Power for the optic detector and the solenoid valve can be fed into the rotating housing through a set of concentric slip rings. There is a practical limit on the number of separate power and signal lines that can be fed into the cassette. Therefore, a second type of valve is preferably used that does not require either power or signal communication to the controllers outside the rotating field. This second type of valve could be a mechanical pinch valve, centrifugally actuated, that would open and close based on the speed of the cassette.

In a preferred embodiment, the stacked co-axial configuration operates as follows: a unit of whole blood is collected in a sterile whole blood bag. This whole blood bag is then connected to a sterile bag set via a sterile connection device. This bag set consists of the bags, tubing, and solutions necessary to separate the unit of whole blood into the desired components. These bags are then positioned in the cassettes in the appropriate cavities. The cassettes are closed and loaded into the centrifuge. Under centrifugal force, the red blood cells sediment radially outward in the whole blood bag. After complete sedimentation, expressor fluid or gas is pumped into the expressor chamber or bag, thereby expanding the flexible membrane or bag that contacts the whole blood bag, which compresses the whole blood bag and forces the supernatant fluid (platelet rich plasma) through the platelet concentrate bag and into the platelet poor plasma collection bag. The expressor fluid or gas can have a density higher than that of blood or lower, including air or other suitable gases. During the routing through the platelet concentrate bag, the platelets sediment to the outer surface of the platelet concentrate bag and are collected. This expression continues until all of the supernatant has been expressed from the whole blood bag and an optical sensor detects the presence of red blood cells in the plasma stream. The valves are then closed and the expressor pump stopped. The centrifuge is then stopped and the cassette removed and opened. The bags can then be separated and placed in the appropriate storage containers.

In alternate embodiments, secondary separation devices, such as, filters, or packed columns, etc., are positioned in-line between the product bags in a manner that allows for the removal of target cells as they move from one bag to another while the cassette is spinning and under the influence of the centrifugal force. Examples of this dynamic, in-line secondary separation would include expressing the PRP supernatant through a first leukodepleting filter as it flows from the whole blood bag to the platelet concentrate collection bag.

Another embodiment of additional expression steps can include those required for filters or packed columns or the like that are only effective when operated statically at zero rpm because the centrifugal force interferes with separation performance. For the PRP example above, the separation steps could be modified as follows: after subjecting whole blood to a soft spin, the PRP is expressed into an attached holding bag that can be sealed closed by a valve until the centrifugal speed is zero. Then, the PRP can be expressed through a first leukofilter or other secondary separation means and into the platelet concentrate collection bag. After a hard spin, the platelets will have sedimented and the platelet-poor plasma can be expressed into the plasma bag.

Another embodiment of static separation is the expression of a storage solution into the red blood cell mass to dilute the red blood cells before expressing the mixture through a leukodepleting filter, all occurring a zero speed.

Other embodiments would preferably use an additional processing step. For example, in one embodiment, red blood cells are first obtained by use of, for example, any of the embodiments set out herein. The red blood cells can then be resuspended in other processing chemicals such as, for example, glycerol, which is used for cryopreservation. The reprocessed red cells can later be passed through a column to remove these processing chemicals. Preferably, a series of washes with special solutions will be used to remove most of the offending process chemicals, and the filter or column will remove the residual traces that remain.

Although it can be advantageous to perform these separation steps in the same centrifuge, it may result in unacceptably long processing times in some cases. Thus, in some embodiments, the secondary separation step takes place outside the centrifuge. Preferably, where the secondary separation step occurs outside the centrifuge, the device further includes a built-in refrigerated chamber for controlling the temperature of the cells during the filtering process.

In some embodiments, other fluids, such as sucrose-based storage solutions that are commonly added to separated blood components, are included in the device through the addition of extra bags and cavities. These bags containing, for example, storage solutions, are in fluid communication with the appropriate blood component bag(s) such that, for example, after the blood components have been separated and collected in the appropriate blood component bag(s), the storage solution can be added to the appropriate blood component bag(s). The number of bags and cavities is limited only by the space available in the centrifuge and the space for flow streams within the cassette.

In accordance with another embodiment of the present invention, a radial segment configuration is utilized. In this configuration, a large rotating drum ("rotor") is divided into pie-shaped segments, each housing a removable cassette comprised of multiple sections. A bag containing the whole blood is placed in one section of the cassette. The remaining sections of the cassette are used for the containment of the separated blood components. For example, in one embodiment, the cassette consists of three segments, wherein the inner segment contains a first expressor chamber, the middle segment contains both a second expressor chamber and a whole blood bag and the outer segment contains a platelet collection bag. A final plasma collection bag can be positioned on an inside surface of the inner segment. Preferably, a pumping device is used to assist in moving fluid and components from one bag to another.

Preferably, an auto-balancing mechanism, which automatically compensates for the changing state of imbalance of the rotor, is connected to the rotor, thereby eliminating the need for additional balancing steps during the separation process.

In yet another embodiment, the bag arrangements presented previously are shaped to fit into a large swinging-bucket rotor. Swinging-bucket rotors have become common in blood component labs and, thus, this configuration would appeal to the market because labs could use the existing installed base of centrifuges for the process and apparatus of the present invention. Modifications could be made to the rotor and the machine to, for example, allow for expressing fluid to enter the bucket and to position valves and optic detectors on the rotor.

Both the radial configuration and the swinging bucket configuration are used in a manner similar to that described above relating to the stacked disk configuration.

FIG. shows the fluid management components housed inside the drive shaft in accordance with one embodiment of the present invention.

FIG. 5 shows the optional processing packs that can be used in the stacked disk configuration in accordance with one embodiment of the present invention.

Figure 3:
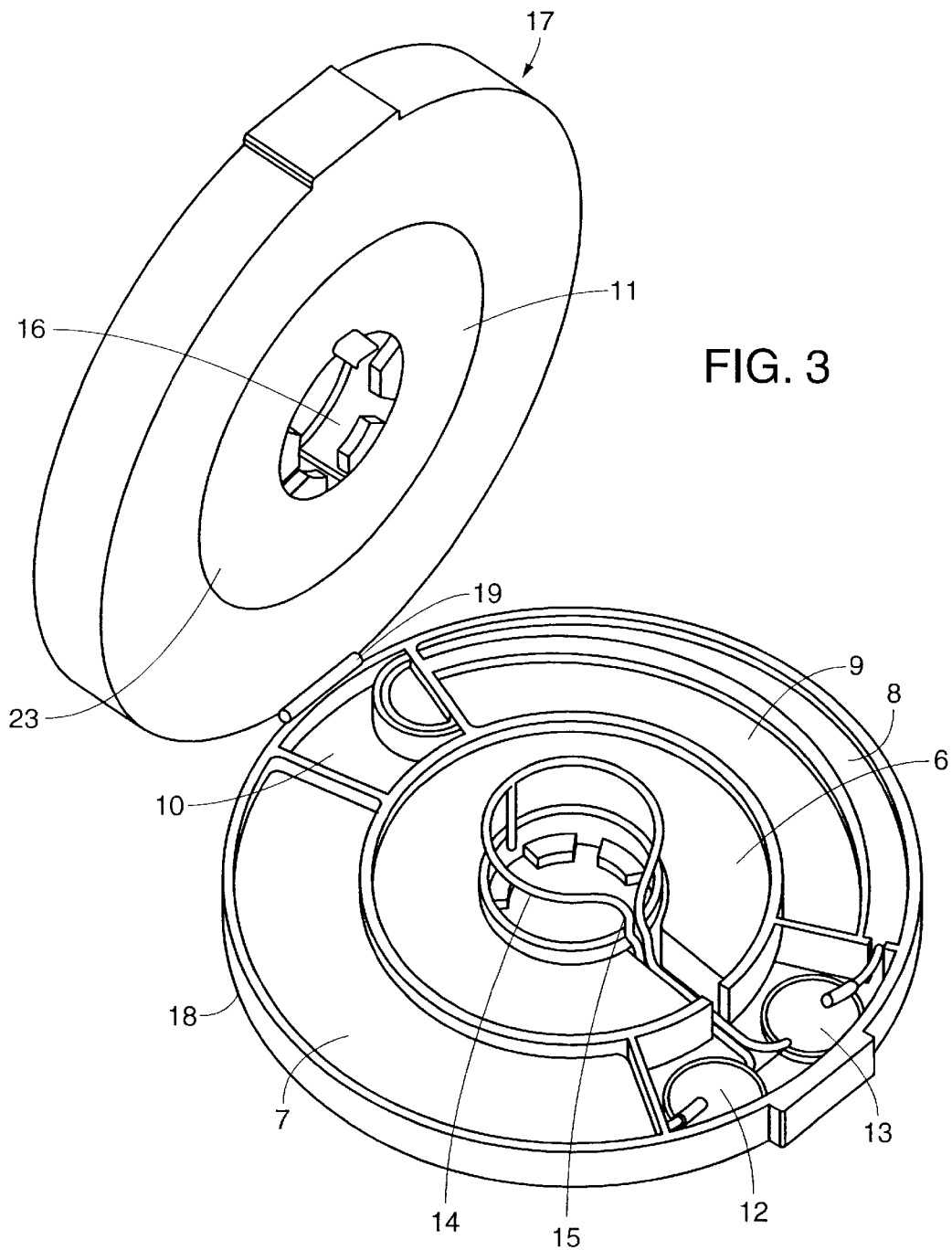
FIG. 3 shows a typical cassette for the stacked-disk configuration in accordance with one embodiment of the present invention.
Figure 4:
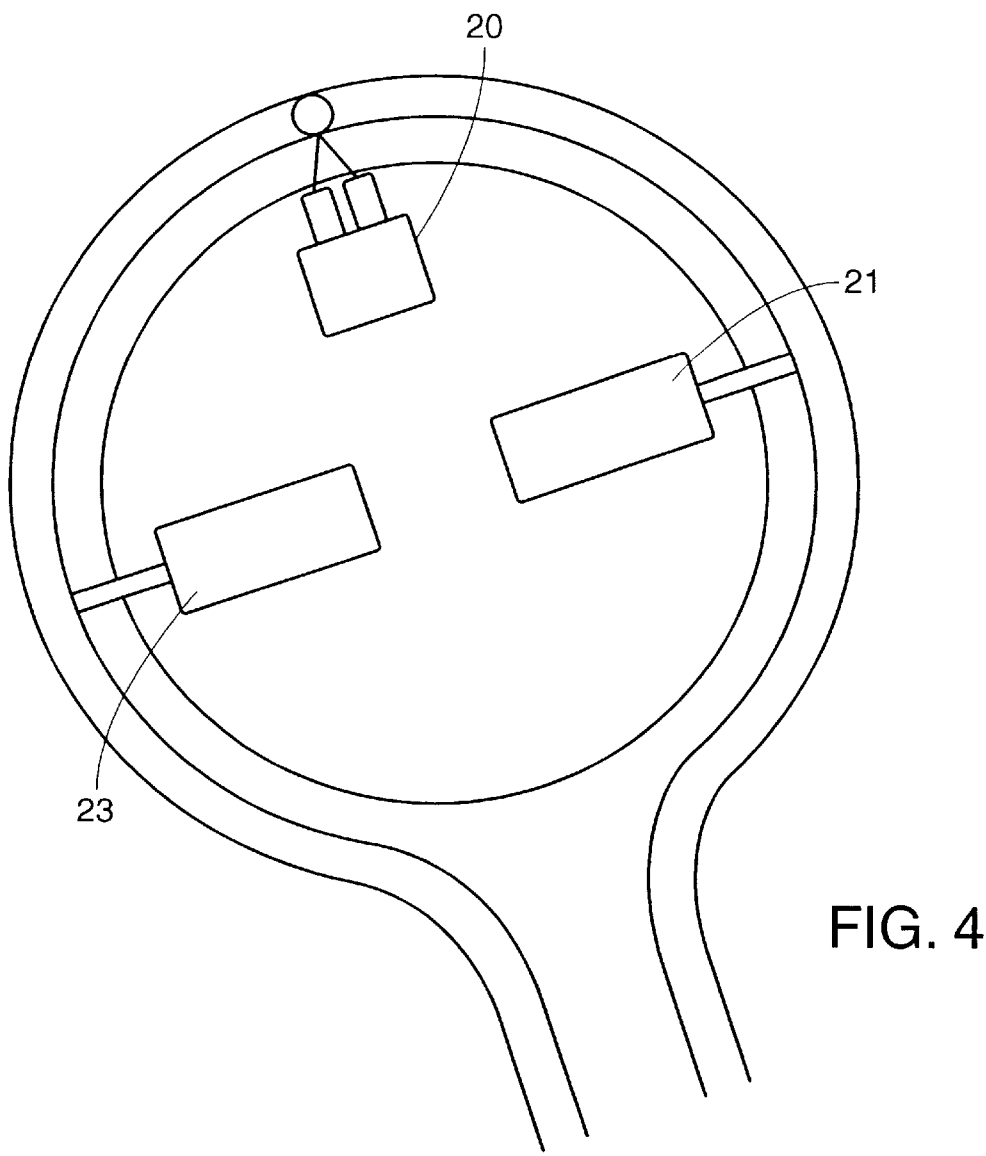
Figure 6:
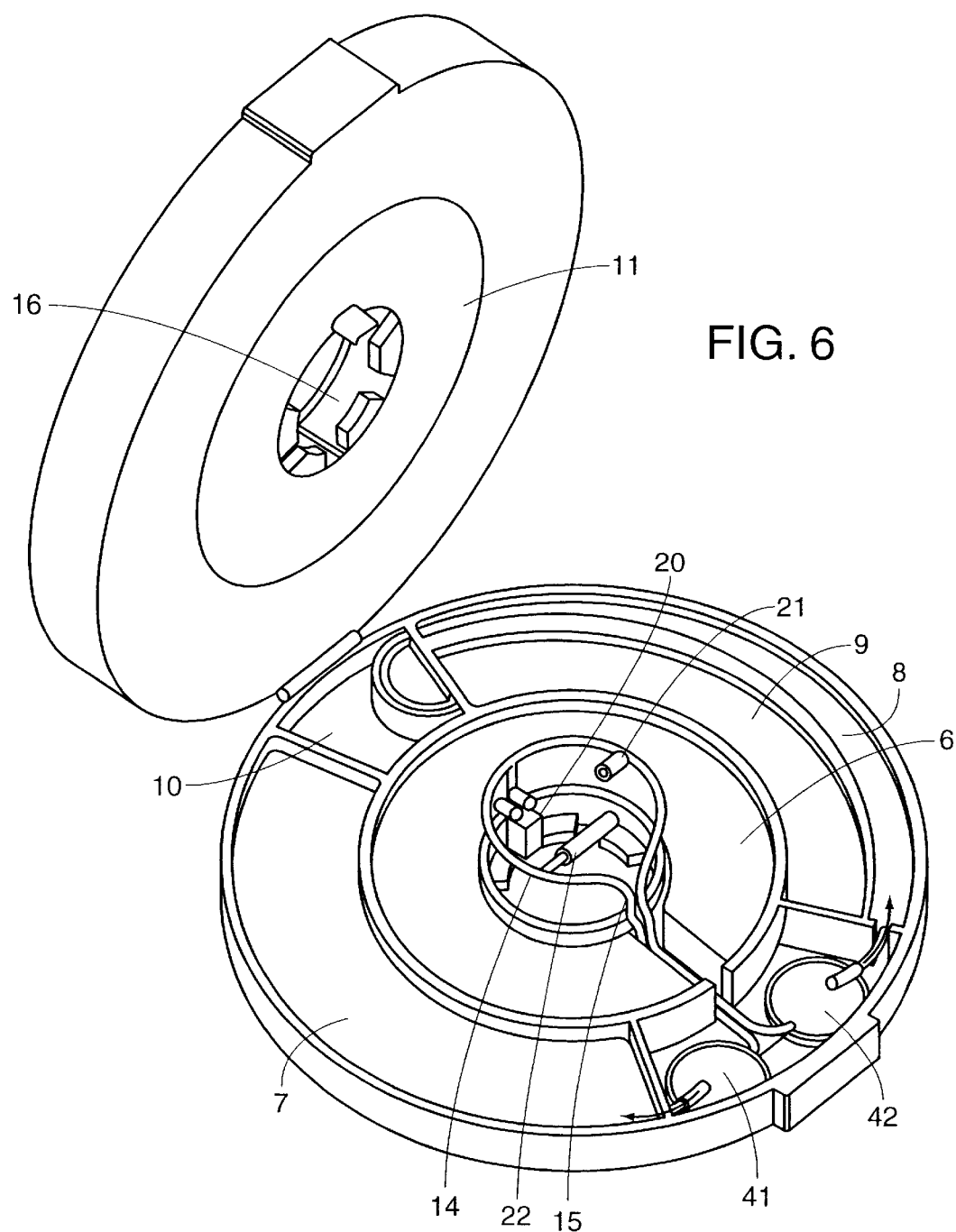

FIG. 6 is the cassette of FIG. 3 including the mechanical components from FIG. 4.

Figure 7:
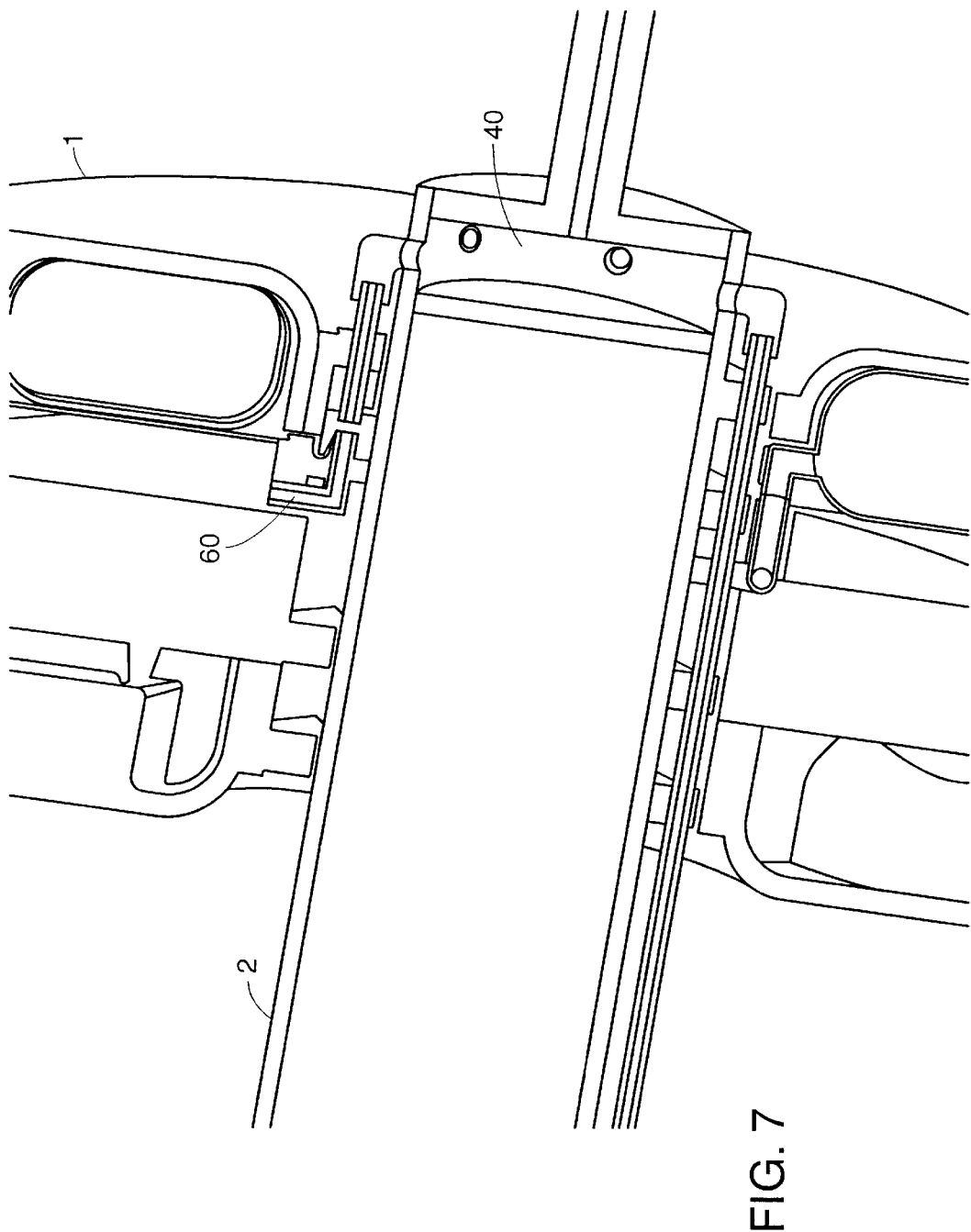

FIG. 7 shows the expressor chamber inside the drive shaft in accordance with one embodiment of the present invention.

Figure 8:
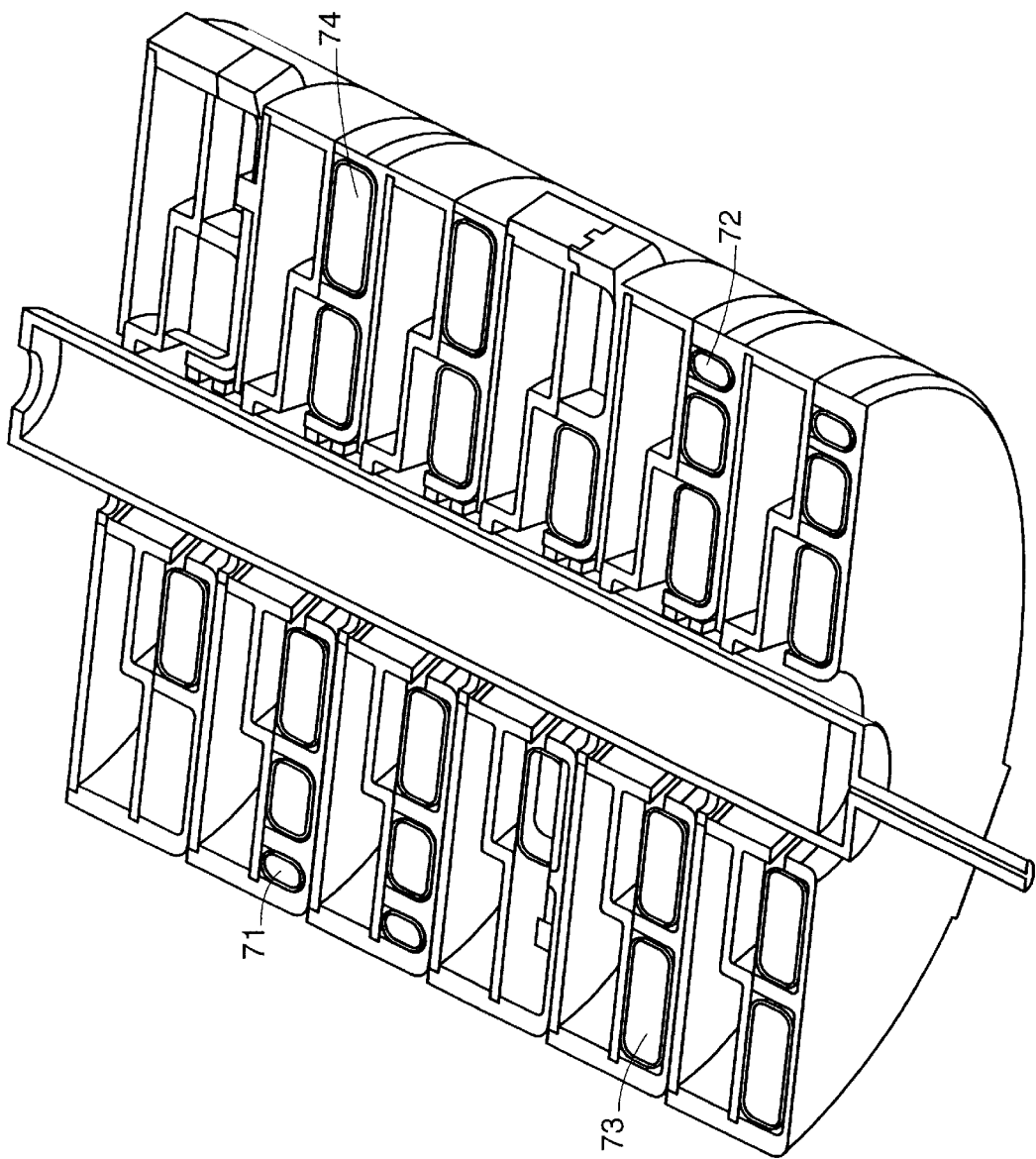

FIG. 8 shows the self balancing feature of the stacked disk in accordance with one embodiment of the present invention.

Figure 9:
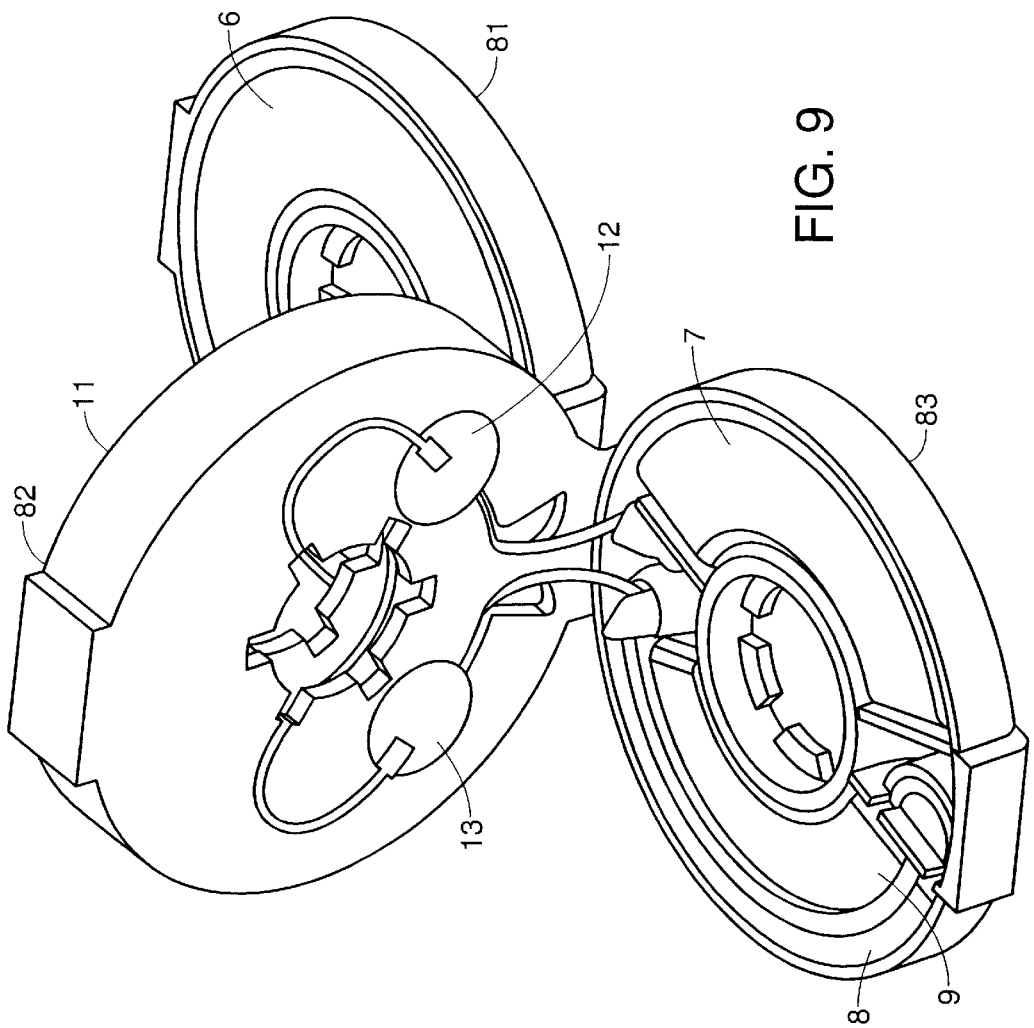

FIG. 9 is a second embodiment of the stacked disk in accordance with the present invention.

FIG. 10 is a third embodiment of the stacked disk in accordance with the present invention.

Figure 11:
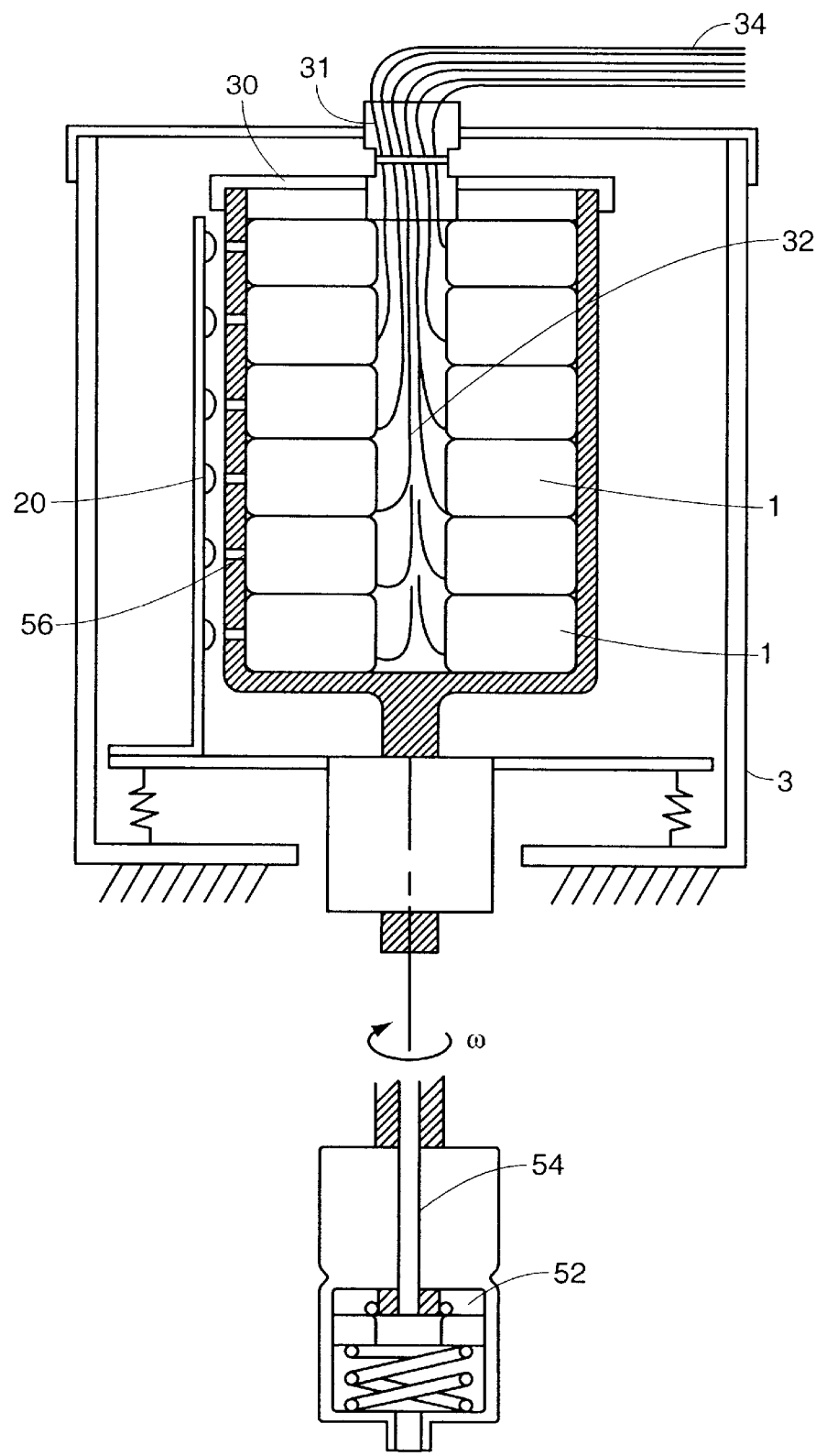

FIG. 11 shows an alternative means for pumping fluids into the cassette in accordance with one embodiment of the present invention.

Figure 12:
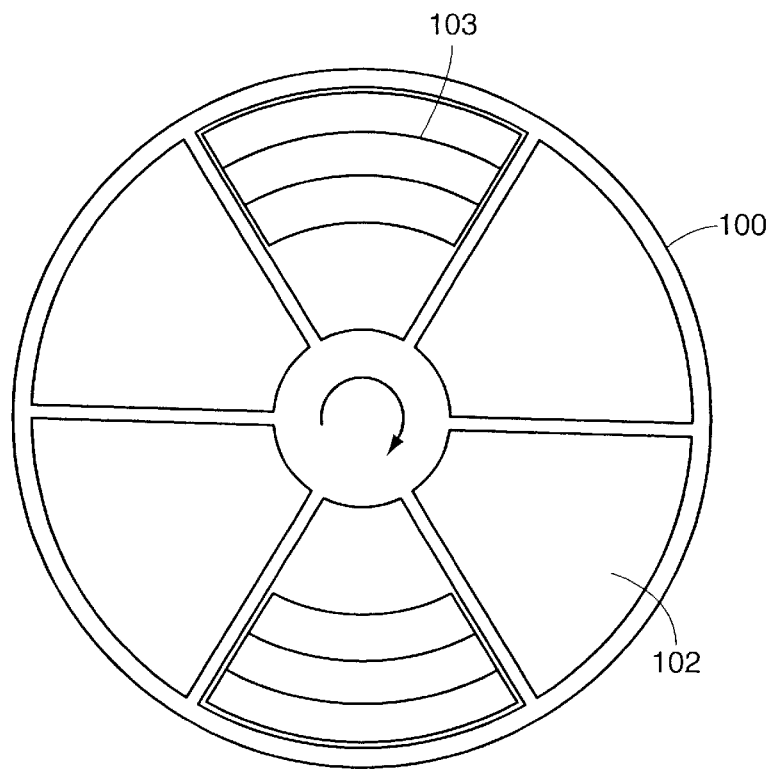

FIG. 12 shows the radial configuration in accordance with one embodiment of the present invention.

Figures 13, 14:
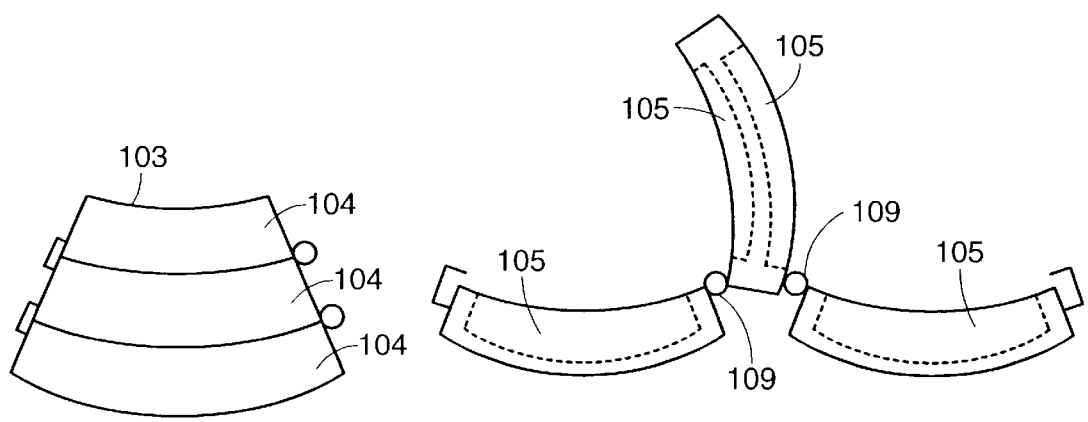

FIG. 13 shows the closed cassette for the radial configuration in accordance with one embodiment of the present invention.

FIG. 14 shows the open cassette for the radial configuration in accordance with one embodiment of the present invention.

Figure 15:
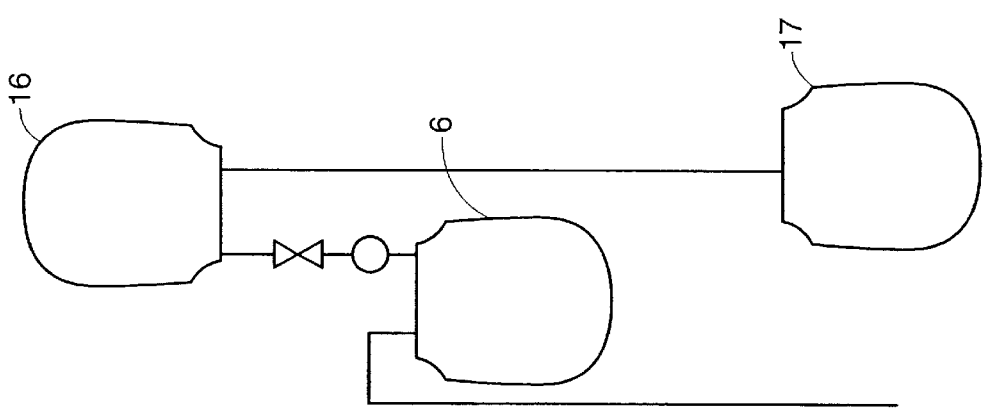

FIG. 15 shows the bag set used in the radial configuration in accordance with one embodiment of the present invention.

Figure 16:
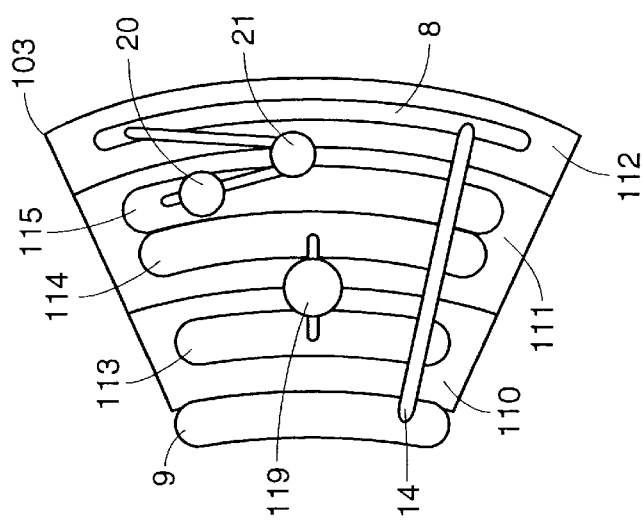

FIG. 16 shows the bag set from FIG. 15 positioned in the cassette of FIG. 14.

Figure 17:
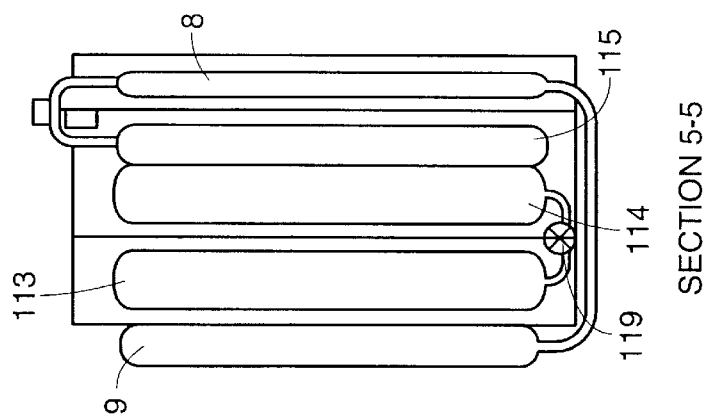

FIG. 17 shows section 5—5 through the cassette in FIG. 16

Figure 18:
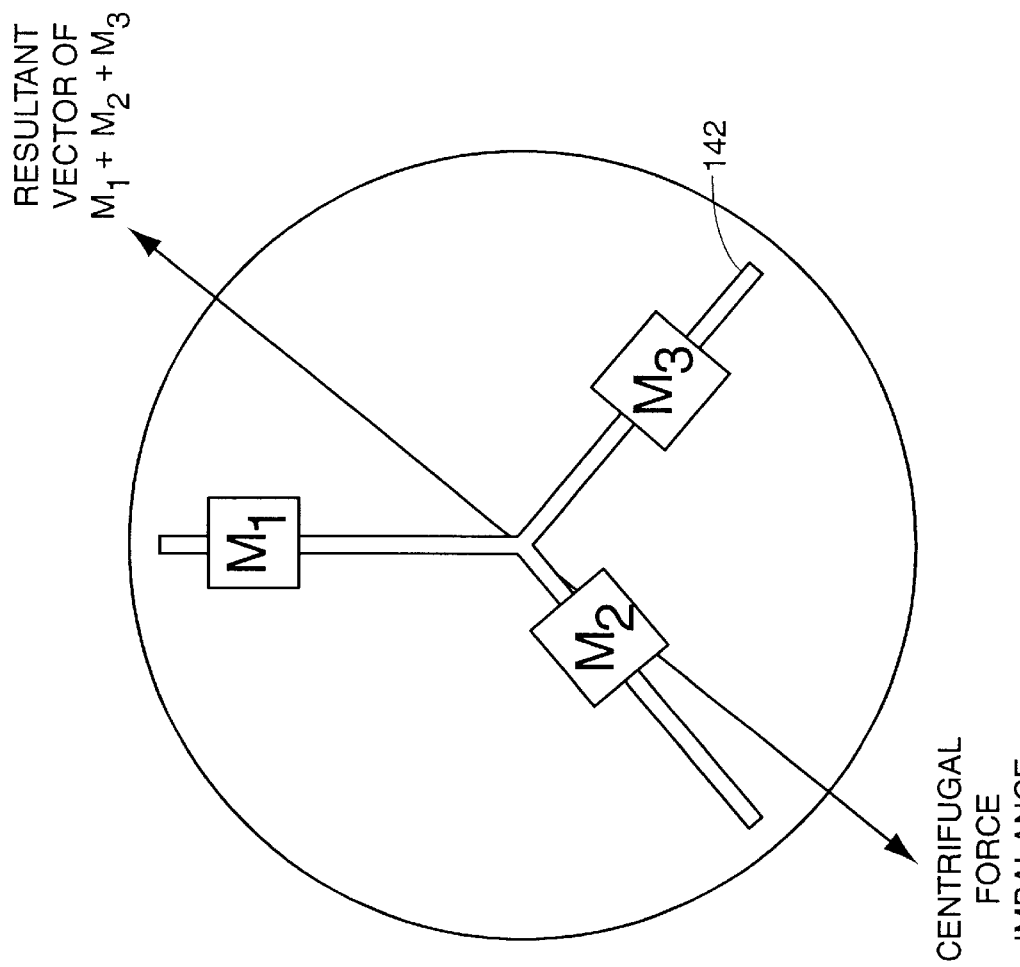

FIG. 18 shows the self-balancing mechanism for the radial configuration in accordance with one embodiment of the present invention.

Figure 19B:
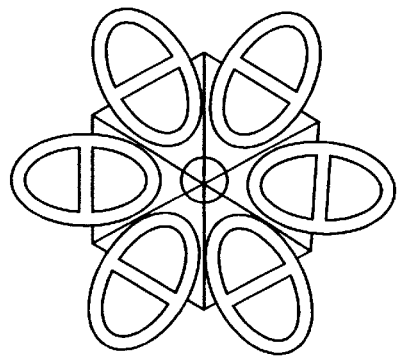
Figure 19A:
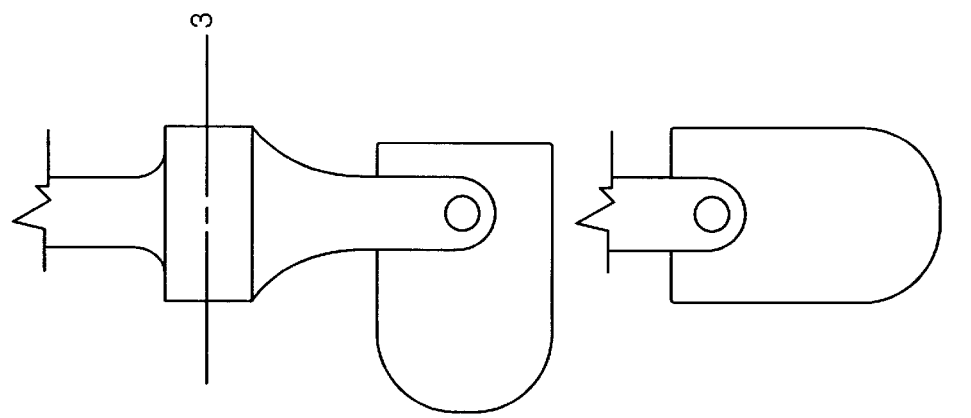
Figure 19:
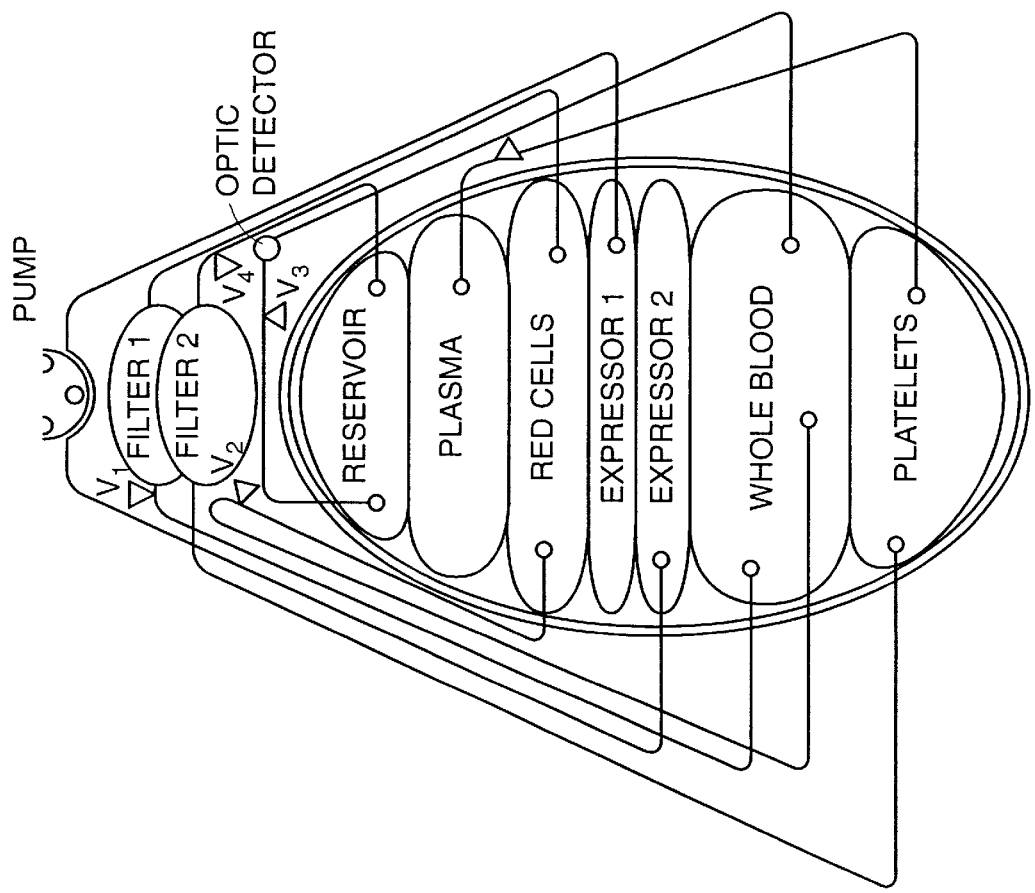

FIG. 19 shows the swinging bucket configuration in accordance with one embodiment of the present invention.

DETAILED DESCRIPTION OF THE INVENTION

Referring now to the various figures of the drawing, wherein like reference characters refer to like parts, there is shown various views of an automated blood component preparation device and methods of utilizing the automated blood component preparation device, in accordance with the invention. The automated blood component preparation device of the present invention separates whole blood into its three primary components, red blood cells, platelets, and plasma. These components are separated and transferred into various blood component bags through sealed lengths of tubing or a similar mechanism that interconnect the various blood bags.

During use of the device, a volume of whole blood is collected and placed into the device. In general, for example, with reference to FIG. 1, the collected whole blood is fed into a whole blood bag 6, which is then placed into the device. Blood component bags, for example, a red blood cell bag 7, platelet concentrate bag 8 and platelet poor plasma bag 9 are also placed within the device and interconnected for separation of the blood components into the appropriate bag. The device holding the whole blood bag 6 is then is spun at high speeds to separate the red blood cells from the plasma. Meanwhile, the spinning whole blood bag 6 is preferably compressed in a way that allows the plasma to move from the whole blood bag 6 to the platelet concentrate bag 8 through tubing that interconnects the whole blood bag 6 and the platelet concentrate bag 8. After filling the platelet concentrate bag 8, the plasma continues to move toward the platelet poor plasma bag 9. The plasma contains a second cellular component, called platelets. As the platelet rich plasma flows through the platelet concentrate bag 8, the platelets sediment radially and collect on the outermost wall, while the platelet poor plasma continues to flow and fills the platelet poor plasma bag 9. This continues until all of the platelet-rich-plasma in the whole blood bag 6 has been squeezed out, or "expressed", from the whole blood bag 6. When this occurs, red blood cells then begin to move out of the whole blood bag 6 until an optic detector 20 senses a color or turbidity shift (or both) and signals valve 21 to close and valve 22 to open. Then, as the expressing fluid or gas continues to squeeze the contents out of the whole blood bag 6, which now contains only red blood cells, these red blood cells flow into the red blood cell bag 7 until all have been expressed from the whole blood bag 6. In red blood cell bag 7, the red blood cells are preferably mixed with a fixed amount of storage solution that is pre-charged into the red blood cell bag 7. Alternatively, rather than adding storage solution to the red blood cell bag 7, the storage solution may be added to the red blood cells in the whole blood bag 6. By adding the storage solution to the whole blood bag 6, the hematocrit, and, therefore, the viscosity of the packed red blood cells is reduced, thereby making pumping of the red blood cells from the whole blood bag 6 to the red blood cell bag 7 less difficult.

The above-described process can also be carried out as an ongoing procedure while the whole blood is being pumped into the whole blood bag 6 from an external source through, for example, a set of rotating face seals or an Adams-type skip rope.

Figure 1:
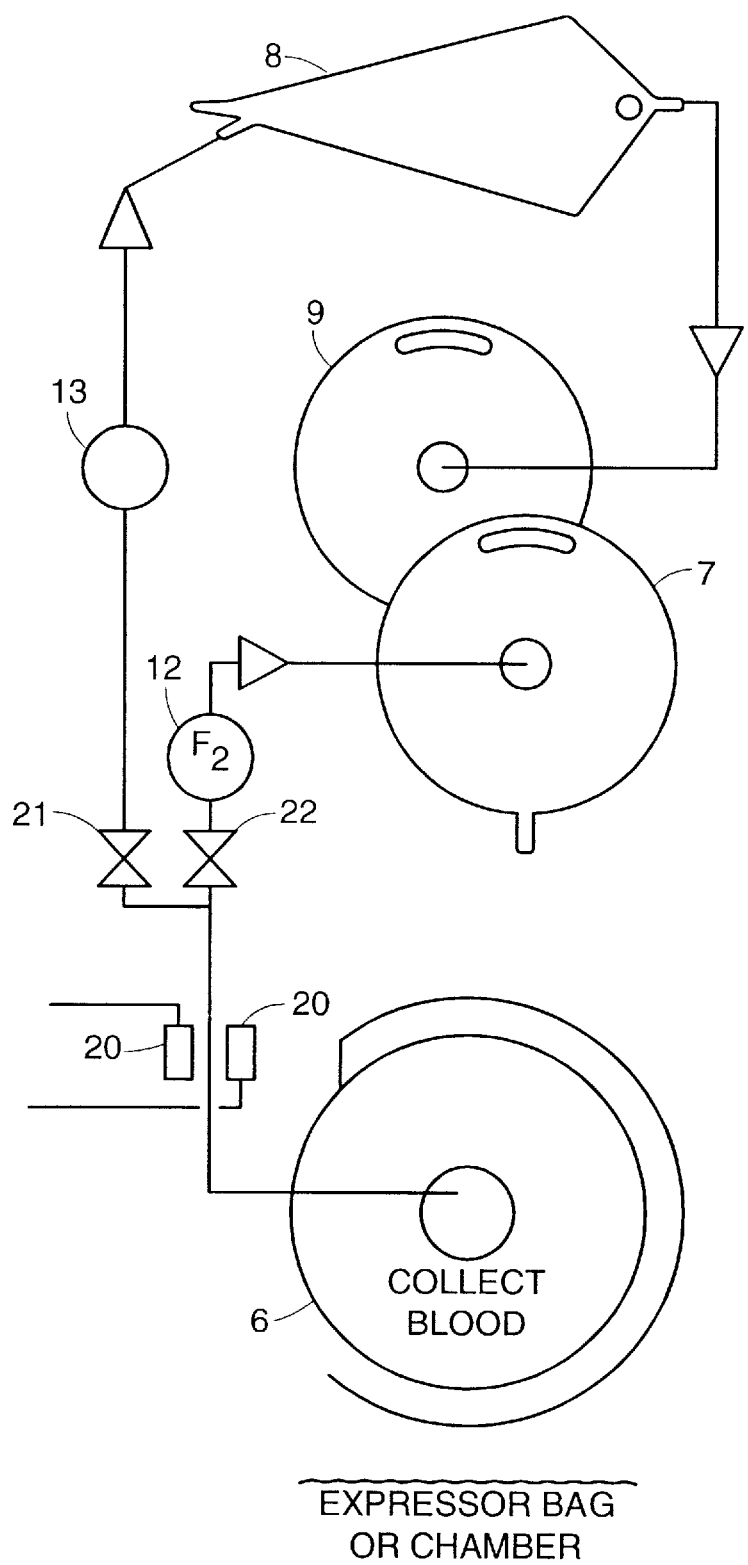
FIG. 1 is a schematic illustration of the separation activities in accordance with one embodiment of the present invention.

Although described with reference to FIG. 1, which contains a whole blood bag 6, red blood cell bag 7, platelet concentrate bag 8 and platelet poor plasma bag 9, it is to be understood that not all of these bags are required for each process, that multiple types of bags may be used and that additional, different bags than those described may be included. Whatever the configuration, however, the design intent is to balance the fluids either within the cassette, between cassettes, or both. In the particular case of that shown in FIG. 1, the bags are circular and stacked vertically so that the fluids are self-balancing as they move from bag to bag. If a bag must be placed off-center, then for any two adjacent cassettes, cassette 1 can be mounted 180° out of phase from cassette 2 for the pair to remain balanced.

Figure 2:
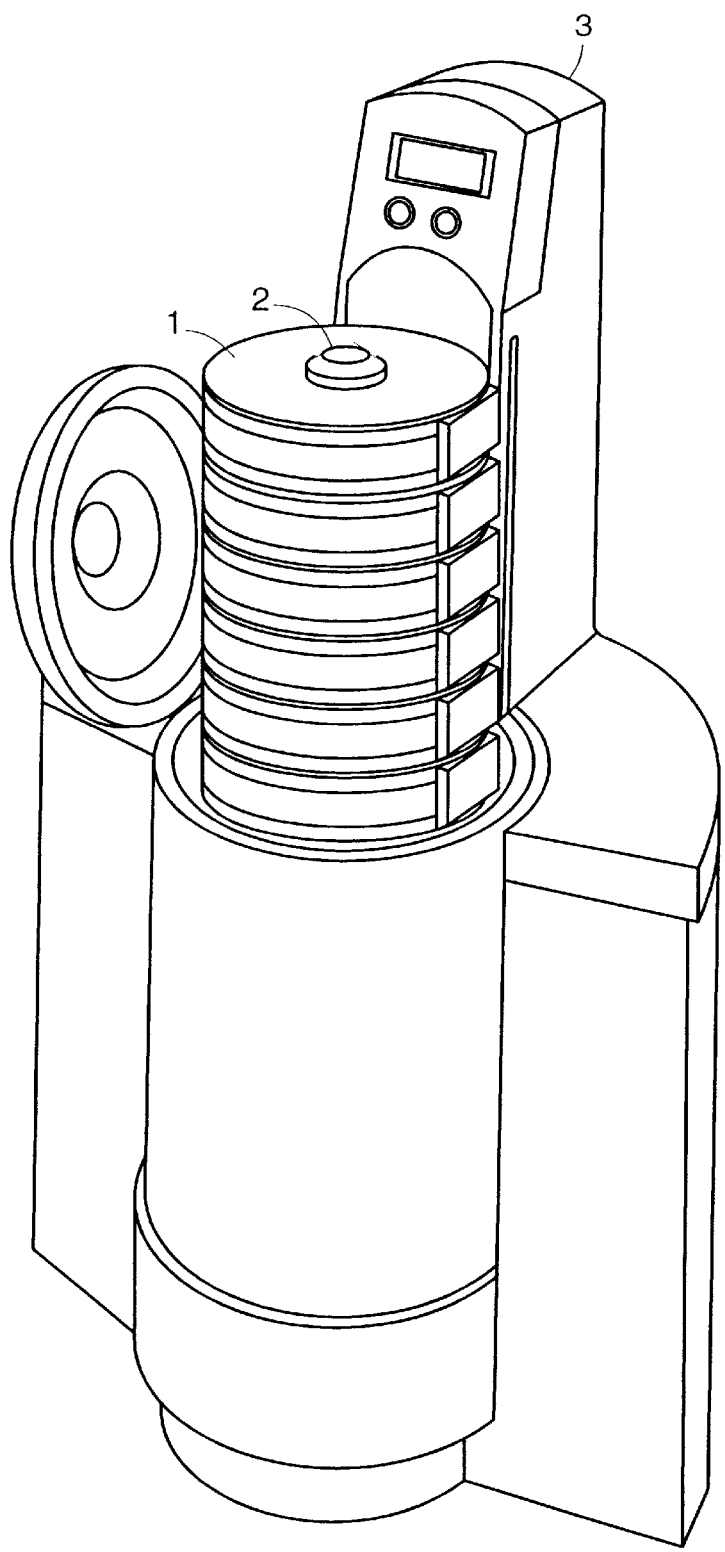
FIG. 2 shows one embodiment of the separation system in accordance with the present invention.

As shown in FIG. 2, an automated blood component preparation device in accordance with one embodiment of the present invention has a stacked co-axial configuration. In this configuration, a plurality of circular cassettes 1 are stacked in a co-axial configuration and placed over a drive shaft 2 within a centrifuge 3, which is designed to accommodate multiple cassettes 1. This configuration is advantageous in that each cassette 1 is self-balancing, as described above, irrespective of the difference in the displaced mass during the expression steps of several cassettes 1 simultaneously.

In one embodiment, the circular cassettes 1 are constructed as shown in FIG. 3, so as to form a plurality of cavities that can be loaded with the whole blood bag 6 and the various blood component bags. For example, as shown in FIG. 3, the various blood component bags may include a red blood cell bag 7, a platelet concentrate bag 8 and plasma bag 9. Other cavities, such as cavity 10, may be included for undefined requirements, such as, for example, holding storage solution that is added to the packed red blood cells and, for example, for holding an expresser chamber or an expresser bag as described in further detail below. Yet other cavities may be positioned to hold filters 12 and 13 (e.g. leukodepleting filters) or separation columns. The cavities can be structured and configured such as those shown in the Figures or in any other manner to permit the various blood bags or other flexible containers, filters and separation columns to be placed into and removed from the cavities.

In addition, the shape of both the cavities and the bags may change to incrementally improve performance. For example, the length and depth of the platelet concentrate bag 8 and the cavity in which it is placed, can be designed such that the smallest platelet entering the cavity is sedimented to the outermost wall before it can be carried by the flow of plasma out of the platelet concentrate bag 8 into the next bag in line, the plasma bag 9. In some cases, it may be advantageous to vary the cross-sectional dimensions of the bags and/or cavities, i.e. the height (axially) and width (radially) in order to cause the fluid flow rate to decrease as materials pass through the bags as shown in FIG. 1. This, for example, can reduce the drag force that moves the platelets through the platelet concentrate bag 8 and, as a result, increase the time that the centrifugal force can act on the platelets to sediment them. Similarly, the radius from the center of rotation of the device to the inner radius of the bags can be gradually decreased as the materials move through the bags. For example, by making the radius from the center of rotation of the device to the inner radius of the platelet concentrate bag 8, sedimentation efficiency is improved as the drag force becomes insufficient to move the platelets radially inward against the centrifugal force vector.

As shown in FIGS. 3 and 6, the blood component bags are in fluid communication with each other with interconnecting tubing 14, or the like. The tubing 14 is preferably positioned in recesses formed (e.g. molded) into the cassette in order to route the tubing 14 between cavities and secure the tubing against the centrifugal force to prevent collapsing or crimping of the tubing walls. A vertical section 15 of the tubing 14, shown in FIGS. 3 and 6, is preferably positioned in the cassette 1 so that it is visible from outside the closed cassette 1. Means for detecting when the blood component preparation process is complete and a means for closing the interconnection between blood component bags also can be located within the device. For example, in one embodiment, as shown in FIGS. 4 and 6, an optic detector 20 can be used wherein the optic detector senses the presence of red cells in the supernatant line of the tubing and signals a valve 21 to close and any pumps (not shown) to stop. This will prevent contamination of the platelet and plasma in bags 9, 8 with red blood cells. Then, valve 22 can be opened and expression can resume to move the red blood cells from the whole blood bag 6 through the tubing 14 and into the red blood cell bag 7. Valves 21 and 23 may be combined into a single valve, e.g. a 3-way valve, and the valves can be either solenoid or motor-driven.

As shown in FIG. 3, the cassettes 1 preferably further include an expressor chamber 23. The expressor chamber 23 is sealed off by a flexible membrane 11. The expressor chamber 23 and flexible membrane are preferably positioned in the cassette 1 adjacent to the portion of the cassette 1 that holds the whole blood bag and blood component bags. For example, as shown in FIG. 3, the cassette 1 may be formed of two separable portions, one of which holds the various blood component bags and the other of which holds the expressor chamber 23. In one embodiment, shown in FIGS. 3 and 6, a top portion 17 is attached to a bottom portion 18 with a fastening mechanism 19, such as a hinge or threaded surfaces along the circumference of the top portion 17 and bottom portion 18, such that the cassette 1 may be opened to expose the inside of the cassette 1. When the cassette 1 is closed, and the device is used, expressing fluid or gas is pumped into the expressor chamber 23 for the purpose of expanding the flexible membrane 11, which pressurizes one or more of the blood component bags. Preferably, when the cassette 1 is closed, the flexible membrane sealing the expressor chamber 23 is in wall-to-wall contact with one or more of the blood component bags. The expressor chamber 23 has a fixed volume such that, as expressing fluid (liquid or gas) is pumped into the expressor chamber 23, the flexible membrane 11 expands against, for example, the whole blood bag 6, thereby squeezing and reducing the volume of the bag 6 and forcing material out of the bag 6. The expressor chamber 23 is preferably supplied with expressor fluid or gas from an external source, preferably through inlet/outlet port 16. Pumping means [not shown] can be located either within the cassette 1 or outside the cassette 1 to further aid in moving materials from one blood bag to another.

In a particularly preferred embodiment, the expressor chamber 23 is positioned such that the flexible membrane 11 is in wall-to-wall contact with the whole blood bag 6. As the centrifuge spins the cassettes 1 at high speeds, the red blood cells are separated from the plasma. Once the separation has occurred, expressor fluid or gas is fed into expressor chamber 23, thereby causing the flexible membrane 11 to expand and compress the whole blood bag 6. This forces the separated plasma to move from the whole blood bag 6 to the platelet concentrate bag 8 through tubing or a similar mechanism that interconnects the whole blood bag 6 and the platelet concentrate bag 8. After filling the platelet concentrate bag 8, the plasma continues to move toward the platelet poor plasma bag 9. As the platelet-rich plasma flows through the platelet concentrate bag 8, the platelets sediment radially and collect on the outermost walls of the platelet concentrate bag 8, while the platelet-poor plasma continues to flow and fills the plasma bag 9. Once all of the platelet-rich-plasma in the whole blood bag 6 has been squeezed out of the whole blood bag 6, only red blood cells remain in the whole blood bag 6. At this time, valve 21 is closed, valve 22 opens and the expressing fluid or gas continues to squeeze the red blood cells out of the whole blood bag 6 into the red blood cell bag 7. Alternatively, it may be advantageous to dilute the packed red cells with storage solution prior to expressing them from the whole blood bag 6.

Alternatively, rather than using an expressor chamber 23, an expressor bag fabricated of a flexible, expandable material may be used.

The number, types and positioning of the interconnected blood component bags may be designed to perform a particular separation activity. FIG. 5 illustrates the configuration of a few of these activities. For example, if only red blood cells and plasma are collected, then a double pack set shown in 5a can be used. If red blood cells, plasma and platelets are collected, then a triple pack set shown in 5b is used. If the packed red blood cells will require additional operations, such as adding chemicals to prepare the red blood cells for freezing, viral inactivation, enzymatic conversion, and the like, then a secondary pack set shown in 5c can be used where the packed red blood cells are temporarily stored in a bag 50 suitable for use in the centrifuge again. Leukodepleting filters 12, 13 that remove leukocytes from the packed red blood cells and platelet-rich-plasma, respectively, can be interconnected in the pack tubing arrangement. In all cases, it is preferable to collect the whole blood into a single whole blood bag 6 without regard for the ultimate activity for which the blood is being drawn. Then, just before processing, the appropriate pack set 5a, 5b, 5c is connected to the whole blood bad 6 by means of a sterile interlocking connector which consists of a female portion 36 sealed into the whole blood bag 6 and a male portion 37 sealed into the pack's connecting tube. Alternatively, a sterile connecting device such as the SCD, which was invented by DuPont and is currently distributed by Terumo Corporation, may be used.

The method of using the stacked coaxial configuration is as follows: units of whole blood are collected in sterile whole blood bags 6. Each of the whole blood bags 6 is then connected, while maintaining sterility, to the appropriate pack set 5a, 5b, 5c, as described above, and the various blood component bags are positioned in the appropriate cavities within the open cassettes 1 as described above. The cassettes 1 are then closed and loaded into the centrifuge 3.

The centrifuge 3 sediments the red blood cells at high speed to the outer portion of the whole blood bag 6. Upon sedimentation of the red blood cells, expressor fluid or gas is pumped into the expressor chamber 23, thereby causing the flexible membrane 11 to expand against the whole blood bag 6. This causes the plasma to flow from whole blood bag 6, past the optic detector 20, through open valve 21, through the platelet concentrate bag 8 to the platelet poor plasma bag 9. As the plasma passes through the platelet concentrate bag 8, platelets are sedimented and collected. The cavity that holds the platelet concentrate bag 8 is preferably sized to limit the amount of liquid held by the platelet concentrate bag 8 to a fixed volume (for example, 50 ml). The expression continues until the optic detector 20 detects the presence of red blood cells exiting the whole blood bag 6. At that time, valve 21 closes and valve 22 opens to prevent red blood cells from passing into platelet concentrate bag 8 and the platelet poor plasma bag 9. Additional valves may be located upstream, for example, valve 22, which may open at this time. Expression then resumes to move the remaining red blood cells from the whole blood bag 6 into red blood cell bag 7. The red blood cell bag may, if desired, be pre-charged with nutrient storage solution for extended storage of the red blood cells.

In some embodiments, secondary separation devices, such as filters 12, 13 (e.g. leukodepleting filters) or columns (not shown), are positioned within with the device in-line between the various blood component bags. These secondary separation devices provide for the removal of target cells as they move from one bag to another. For example as the platelet rich plasma is expressed from the whole blood bag 6, it can be forced through leukodepleting filter 13 at a rate that optimizes the filter's performance. One variable in this optimization is the rate at which the cells flow through the filter media. This flow rate is well defined and is equal to that rate established as a bag of packed red blood cells at 4° C. is drained through the filter by gravity from a height of three feet. This rate can be reproduced in a high g-force centrifugal field by positioning the filter housing such that the flow vector is directed exactly counter current to the direction of the centripetal force vector. The resultant force vector acting on the red blood cells, then, is the difference between the drag force from the pumping fluid carrying the cells radially inward and the centripetal force moving them radially outwards. This orientation is contrary to that shown in FIGS. 3 and 6, which rely solely on the pumping rate to control the flow rate across the filter media.

Similarly a leukodepleting filter 12 may also be placed inline with the inlet to the red blood cell bag 7. If necessary, the inlet and outlet axis of either or both filters 12, 13 may be positioned radially rather than tangentially as shown if FIG. 6, so that the centrifugal force does not cause the fluid flow to be biased towards the radially most outboard position within the filter housing. In another embodiment, a column designed for the collection of stem cells is positioned between the whole blood bag 6 and the plasma bag 9 such that the column collects CD-34 stem cells from the plasma stream as it is being expressed from the whole blood bag 6 to the plasma bag 9. In another embodiment, a column may be positioned in line with the red blood cells such that the red blood cells are passed through the column to remove residual processing chemicals (e.g. glycerol, which is used for cryopreservation).

Alternatively, these secondary separation steps may take place outside the centrifuge. Preferably, where the secondary separation steps occurs outside the centrifuge, a built-in refrigerated chamber (not shown) is included for controlling the temperature of the cells during the filtering process.

The expressor fluid or gas, as shown in FIG. 7, may be transferred to the expressor chamber 23 from an external source through the inlet/outlet port 16, which, in turn, is in fluid communication with a common supply header, 40, positioned within the drive shaft 2. Cassettes 1 are preferably positioned onto the drive shaft 2 in pairs so that one is 180° from the other as shown in FIG. 8. In this configuration, the plasma 71 that is expressed to the side of one cassette is mechanically balanced with the plasma 72 moving to the opposite side of the adjacent cassette. Similarly, the red blood cells 73 that are expressed to one side of one cassette are mechanically balanced by the red blood cells 74 moving to the opposite side of the adjacent cassette.

The configuration of the cassettes 1 is not limited. For example, FIG. 9 shows a configuration where the cassette 1 is comprised of three segments: top segment 81 holds the whole blood bag 6, middle segment 82 holds the expressor chamber 23, flexible membrane 11 and filters 12, 13, and bottom segment 83 holds the platelet concentrate bag 8, the platelet poor plasma bag 9, and the red blood cell bag 7. This is advantageous in that the cassette 1 can be made more compact and can be used in a small, portable centrifuge where the diameter of the cassette 1 can be as small as 5–6 inches. Alternatively, the three segment cassette can made larger, for example 12 inches in diameter, in which case the cassette 1 could carry over three liters of fluids in addition to the volume of the cells. This may be useful if a secondary processing of the packed red blood cells requires large amounts or processing fluids. As an example, the deglycerolization of frozen red cells requires that approximately two liters of solutions be used to wash the cells before transfusion; hypertonic 12% NaCl, 1.6% NaCl, and resuspend in 0.9% saline with dextrose (Method 9.6 of the AABB Technical Manual $12^{th}$ Edition). In this case, the three solutions can be carried "on board" to sequentially wash the red cells, loaded into the bags 7, 8, and 9 in FIG. 9. Two expressor chambers 23 would be used to move the cells into and out of the red blood cell bag 7, and an additional valve would be added. Preferably, a common centrifuge would be used to process a multiplicity of cassette styles, each performing a different blood processing activity in the blood center. Other examples include the washing or rejuvination of red cell cells (Method 9.5 of the AABB Technical Manual $12^{th}$ Edition) that requires 2 liters of unbuffered 0.9% saline, virally inactivated cells (approximately 2 liters), enzymatic conversion of red cells (approximately 3 liters), and others.

Another variation of the radial configuration cassette is shown in FIGS. 10. This configuration contains a top portion 17 and a bottom portion 18. In this configuration, in the bottom portion 18, the red blood cell bag 7 and platelet poor plasma bag 9 are positioned to be coaxial with each other and the whole blood bag 6. The blood is collected and subsequently connected, while maintaining sterility, to a processing bag set, e.g. FIG. 5, in the same manner as described above with the exception that as the bag set is positioned into cassette 1, the placement of the bags varies. In the bottom portion 18, the whole blood bag 6 and expressor chamber 23 are placed into a cavity of the cassette. This chamber is in fluid communication with a supply of expressing fluid 39, the pressure of which is controlled by a pumping means outside of the cassette. The top portion 17 of the cassette is placed over the bottom portion 18 to enclose the whole blood bag 6. The top portion 17 contains cavities for the red blood cell bag 7, platelet poor plasma bag 9, and the platelet concentrate bag 8. Cavities can also be provided for one or more filters. As shown in FIG. 10, for example, a platelet rich plasma filter 42 and a red blood cell leukofilter 41 are positioned in the cassette 1 as shown. Channels are preferably provided to fix the routing of the interconnecting tubing 14 so that sensors (such as optic and pressure sensors) and valves 21 can reliably contact the tubing 14. These sensors and valves can be positioned within the cassette 1, or, preferably outside the cassette 1 as part of the centrifuge drive mechanism.

Another embodiment of the invention pumps the whole blood (or other cell mass) into the cassettes 1 while the separation is taking place. For example, in FIG. 11, multiple lumens (tubes) 34 are connected to the separation chambers of one or more cassettes 1 housed in a centrifuge 3 preferably through either of two means: a multichannel face seal or an Adams-type skip rope. The separation proceeds as described above, except that the additional blood that is continuously being pumped into the device displaces and forces the platelet-rich plasma out of the whole blood bag 6. Then, as described above, when only red blood cells remain in the whole blood bag 6, expresser fluid or gas can be pumped into the whole blood bag 6 through rotating seals 52 and feed tube 54 located in at the bottom of the centrifuge 3. Similarly, if the expresser fluid or gas is removed from the whole blood bag 6, then additional fluids can be added to the cell mass in the whole blood bag 6 via the rotating seal 52 or multiple lumens (tubes) 34 and removed with the expresser fluid or gas as it is again pumped into the whole blood bag 6. In this configuration, the liquid that is expressed after the components have been separated can be expressed out of the whole blood bag 6 through any one the multiple lumens (tubes) 34 and into a waste bag. The number of cassettes is limited only by the strength of the closing mechanism that secures the cassettes 1 in the closed position during separation and the size of the centrifuge. If a small device is required, as few as one cassette can be used. If high throughput is required, a plurality of cassettes can be used.

Shown in FIG. 11 is an alternate method for positioning the optics to detect the red blood cell interface during expression. In this case, the optic sensor 20 is fixed to the non-rotating containment wall of the centrifuge 3. The optic sensor 20 monitors the tubing 14 in the cassette 1 through a hole 56 in the cassette 1 that allows visualization of the length of tubing 14 that carries the plasma and red blood cells from the whole blood bag 6 to the platelet concentrate bag 8. The sampling rate of the optic sensor 20 is such that it emits and receives an optic signal in less time than that which is required for the hole 20 to rotate past its field of view.

As shown in FIGS. 12–14, an automated blood component preparation device in accord with another embodiment of the present invention has a radial segment configuration. In this configuration, a large rotating drum or a rotor 1, is divided into pie-shaped segments 102. Into each segment 102, a cassette 103 having a shape conforming to the radial segment configuration of the rotor can be inserted. The cassette 103 is comprised of a plurality of sections 104, and each section can contain one or more cavities 105 for the containment of the fluids necessary to effect the blood component preparation process. Cavities 105 can be structured and configured such as those shown or in any other manner to permit whole blood bags and various blood component bags or other flexible containers to be placed into and removed from the cavities 105.

The bags set, including the whole blood bags 6, are then loaded into the cavities 105 in the cassette 103 (FIG. 12). The number of sections 104 and cavities 105 required depends on the number of bags used in a given process. Once the bags are loaded into the cassette 103, the cassette 103 is closed. A lid (not shown) of the cassette 103 can be attached, for example, on one side of the cassette with hinges or other fastening means (not shown) so that the cassette can be opened to expose all cavities and shut quickly. As shown in FIGS. 13 and 14, the sections 104 can be connected with hinges or other fastening means 109 that allows the sections 104 to be separated from each other to expose the cavities 105.

In one preferred embodiment shown in FIG. 16, the cassette 103 consists of three sections: an inner section 10, a middle section 111 and an outer section 112. The inner section 110 typically contains a first expressor reservoir 113 into which an expressor bag 7 can be placed. The middle segment 111 contains both a second expressor reservoir 114, into which an expresser bag can be placed and, adjacent to the expressor reservoir, a whole blood cavity 115 into which a whole blood bag 6 can be placed. The outer segment 112 contains a cavity for a platelet concentrate bag 8. A final plasma bag 9 is positioned on the inside surface of the inner segment 110, as shown in FIG. 16. The bags are interconnected by tubes 14 that allow fluid to flow from one bag to another. A pumping means 119 can further be located within the device to aid in moving fluid and components from one bag to another. A means for detecting when the blood component preparation process is complete and a means for closing the interconnection between bags also can be located within the cassette. For example, an optic detector 20 can be used, which senses the presence of red cells in the supernatant line and signals a valve 21 to close and the pump 119 to stop. This will prevent contamination between the contents of the various bags.

Various configurations of conventional valve designs can be used. For example, two individual valves can be used that are either electronically powered or centrifugally actuated. A single, electronic two-way valve can be used in place of two separate valves to take up less space and add fewer power leads. The valves that are centrifugally actuated are preferred where it is desirable to eliminate the need for power connections The expressor bags that are used within the cassette 103 are preferably fabricated of a material that allows them to expand and contract repeatedly to move fluids between the bags. Preferably, the expressor bags are fabricated of an elastomeric material such as, for example, silicone or natural rubber. The expressor bags can be permanently installed in the cassette or, preferably, are removable.

The whole blood bags 6 are sterile bags into which whole blood is drawn and processed. The whole blood bags 6 are fabricated of any type of material generally accepted and approved for that purpose. Preferably, the whole blood bags 6 are sized and shaped to fit readily into the appropriate cavity. However, any shape may be used provided the whole blood bag 6 fits within the appropriate cavity of the cassette 103.

The number of cassettes 103, sections 104 and cavities 105 can vary depending on design choice. For example, fewer or more cassettes 103, sections 104 and cavities 105 can be used depending, for example, on the number of whole blood bags being fractionated and the number of components into which the whole blood is to be separated.

The method of using the radial segment configuration is as follows: units of whole blood are collected in sterile whole blood bags 6. The whole blood bags 6 are then positioned in the appropriate cavities 105 within the cassettes 103 as described above. The cassettes 103 are closed and loaded into the segments 102 in the centrifuge 3. Under centrifugal force, the red blood cells sediment radially outward in the whole blood bag 6. After complete sedimentation, expressor fluid or gas is pumped from the first reservoir 113 to the second reservoir 114, which compresses the whole blood bag 6 and forces the supernatant fluid (platelet rich plasma) through the platelet concentrate bag 8 and into the plasma bag 9. During the routing through the platelet concentrate bag 8, the platelets sediment to the outer surface and are collected in the platelet concentrate bag 8. This expression continues until all of the supernatant has been expressed from the whole blood bag 6. When this occurs, an optic detector 20 senses the presence of red cells in the supernatant line and signals a valve 21 to close and the expressor pump 119 to stop. This prevents any red cells from contaminating the downstream bags. The centrifuge can then be stopped and the cassettes 103 removed and opened. The bags are then separated and placed in the appropriate storage containers.

In a preferred embodiment, filters or packed columns or other secondary separation devices are positioned such that when the blood component bags are removed from the device, they have attached to them the secondary separation device and a receiving/storage bag. This allows the product bag to be hung in a temperature-controlled environment and the product slowly gravity drained through the secondary separation device into the final receiving/storage bag, which might contain nutrient solutions for long-term storage. In this configuration, the centrifugal forces would not interfere with the function of the filter or column and the secondary separation step, which is relatively slow, does not tie up the centrifuge, thereby increasing throughput. In some cases, it is preferable to perform the secondary separations in line within the cassette without the double handling mentioned above. In such embodiments, the secondary separation devices are positioned in line such that separation would occur as the fluids are expressed from one blood component bag to another as set out above. For example, filters or columns can be positioned between the blood component bags, as set out above, to provide for the removal of target cells as they move from one blood component bag to another.

In other embodiments, other fluids, such as sucrose-based storage solutions, can be included through the addition of extra bags and cavities. The number of bags and cavities is limited only by the space available in the rotor segment and the safety of flow streams within the cassette. Thus, any number of bags, sections 102, cassettes 103, segments 104 and cavities 105 is within the scope of the invention.

The present invention preferably has an auto-balancing mechanism 142, shown in FIG. 18, connected to the centrifuge 3. Thus, manual balancing of loads, which is typically required when using conventional devices, would not be required. During blood component preparation, it is unlikely that the mass center of each cassette 103 will be in balance with the other segments 102. It is further unlikely that the fraction of supernatant that is moved from one location to another will be equal in both the volume and the rate that would be necessary to keep the segments 102 in balance after the start of the expression step. Thus, an auto-balancing mechanism 142 continuously compensates for the changing imbalance.

It is common to fix accelerometers to centrifuge assemblies to define the magnitude and the angle of the resulting imbalance vector for a rotating body such as that described herein. Similar accelerometers can be fixed to the centrifuge frame that supports the centrifuge 3 of the present invention. These accelerometers are positioned to capture readings only in the single plane of the bottom surface of the centrifuge 3. A software algorithm then can be used to interpret this data, calculate the magnitude and angle of the imbalance, and signal a set of three linear actuator motors, as shown in FIG. 18, to move to a calculated position that results in an opposing force equal and opposite to that experienced from the imbalance. This effectively cancels out the imbalance effects and assures smooth running and reliable separation of the cells from the suspending plasma. Other mass distribution methods for canceling the imbalance also can be employed, such as pumping compensating fluid volumes to specific centrifuge locations.

In another embodiment, the set of blood component bags is configured to fit into an existing piece of equipment that is already in the blood separations laboratory. FIG. 19A shows the layout of a multiple bucket set, while FIG. 19B illustrates a typical way to apply the aforementioned inventions to this swinging bucket. This embodiment operates to separate the blood components in a manner similar to the embodiments set out above.

Irrespective of the type of separation device that is used, i.e. stacked disc, radial segment, or swinging bucket, the automated processing steps and the retention of critical process data are controlled by a micro-computer-based logic controller.

In general, the logic controller consists of at least one micro computer (microprocessor) embedded within the centrifuge 3 and the electronic circuitry required to interface it with the data input and the data output of the system. In this case, the input might include such data as the number of cassettes 1, the position of each cassette 1, and which bag set has been installed in the cassettes 1. Based on this input, the controller calculates the output response. This operating output would include the automated sequence of commands that separate the components, including the rotational speed, time, temperature, optical clarity of the supernatent, valve state, etc. In addition to this operating output, the controller also outputs to a memory device interface the information that must be recorded for each unit. The data is retained as part of the lot history record for each unit of blood and includes the following:
1. Donor ID number
2. Bag set part number and lot code
3. Filter part number and lot code.
4. Packed red cell bag ID number
5. Platelet concentrate bag ID number
6. Plasma bag ID number
7. Operator number
8. Purity of platelet concentrate (an optical reading)
9. Operating parameters, including:
   a. Time lag of whole blood
   b. Temperature profile
   c. Speed profile
   d. Valve position as a function of time All of this is information is used to validate that the component manufacturing process is being adequately controlled and that each unit of blood has a manufacturing lot history record that documents that it met all release criteria. This includes the information necessary to recall a component if the donor is rejected or if a lot of defective components is found to have been part of the processing sets.

A preferred mechanism for controlling both the input and output of all of this information is to embed a micro-digital UHF ID tag (not shown) in the label of each whole blood bag 6 and blood component bags. When the bags are positioned within the cassettes 1, the tags are preferably positioned to be read from outside the cassette 1. When the cassette 1 is slid into place in the separation device, an electronic reader records the information that is contained on each UHF ID tag as it passes by. The donor ID number is now irreversibly linked to the lot numbers of all of the components that will be involved in the separation process and the centrifuge controller knows the position of that cassette 1 and the protocol with which it will be processed. During the separation process, the critical operating parameters will be recorded, including the time and speed profiles, the optical purity of the supernatant, and that the sequence of the series of process steps were accomplished and were within the validated limits of each variable. For example, if the first soft spin is programmed to be 2,000×G for 2 minutes, the actual speed and time will be recorded and compared with the validated limits. If the speed is outside these limits, a warning can, for example, be recorded for each cassette 1 and will also appear to the operator on the operating screen of the device and in the data base. Further, if the time between collection and separation exceeded AABB standards, a digital warning, for example, could be issued that would preclude the operator from getting a human readable label until the discrepancy is resolved. Further, if the operator had not been trained and pre-qualified to operate the system, a warning could be issued and the problem resolved before the centrifuge would accept the command to begin the separation process. These examples exemplify the type of the data required to validate the separation manufacturing process.

As the component bags are removed from the cassette 1, the information in the UHF ID tag will then be compared to release limits and, if acceptable, used to print labels that will be affixed to each bag. These labels may include human-readable ID numbers and bar codes for the transfusion centers that cannot read the UHF ID tag in the label of the component bag. The transfusion centers will then write certain information on the UHF ID tag including time and location of receiving, the time of transfusion and the recipient ID number. This completes a "chain of custody" record from the donor to the recipient for each unit of blood.

If the information on the UHF ID tag is not within accepted limits, the unit can be quarantined for further assessment by a trained Quality Assurance staff.

Alternative means may be used to transfer data from the bag set within the cassette to the centrifuge logic controller. For example the data base may employ optic sensors, such as bar code readers, to transfer the data as the cassette is being slid into place.

Although the present invention has been described in detail including the preferred embodiments thereof, such description is for illustrative purposes only, and it is to be understood that changes and variations may be made without departing from the spirit or scope of the following claims.

What is claimed is:

1. An automated device for separating blood into its components comprising:
   one or more cassettes;

a plurality of cavities in each cassette for housing a whole blood bag and at least one blood component bag;

the whole blood bag and blood component bags in fluid communication with eachother;

wherein the one or more cassettes are stacked in a co-axial configuration in the centrifuge;

wherein the one or more cassettes are placed into a centrifuge and, as the centrifuge spins the one or more cassettes, whole blood in the whole blood bag separates into its components, and the components are caused to flow into different blood component bags.

2. The device of claim 1, a plurality of cassettes are supplied with whole blood and multiple units of blood are separated into their components simultaneously.

3. The device of claim 2, wherein the cassettes are circular.

4. The device of claim 1, wherein each cassette further comprises an expressor bag or expressor chamber sealed by a flexible membrane, whereby the expressor bag or the flexible membrane is in contact with the whole blood bag and/or at least one blood component bag, whereby as expressor fluid or gas is fed into the expressor chamber or expressor bag, the flexible membrane or expressor bag expands against the whole blood bag and/or at least one blood component bag, thereby compressing the whole blood bag and/or at least one blood component bag to force separated blood components to flow into different blood component bags.

5. The device of claim 4, wherein each cassette comprises at least a top portion and a bottom portion, the expresser bag or the expresser chamber and flexible membrane, plurality of cavities and the whole blood bag and blood component bags situated in the portions such that the whole blood bag and blood component bags are in fluid communication with each other and the expressor bag or the expressor chamber and flexible membrane are positioned in contact with the whole blood bag and/or at least one blood component bag.

6. The device of claim 5, wherein the top portion houses the expressor bag or the expressor chamber and flexible membrane and the bottom portion housing the plurality of cavities and the whole blood bag and blood component bags.

7. The device of claim 6, wherein the bottom portion further houses one or more filters.

8. The device of claim 5, further comprising at least one middle portion.

9. The device of claim 8, wherein the middle portion houses the expressor bag or expressor chamber and flexible membrane, the top portion houses the whole blood bag and the bottom portion houses the blood component bags.

10. The device of claim 9, wherein the middle portion further houses one or more filters.

11. The device of claim 8, wherein the top, bottom and middle portions are removably connected to provide access to the interior of the cassette.

12. The device of claim 8, wherein the top, bottom and middle portions are connected with a hinge.

13. The device of claim 1, wherein the whole blood bag and blood component bags are interconnected with tubing.

14. The device of claim 1, wherein the cassettes are self-balancing as the blood components move from one cavity to another.

15. The device of claim 1, further comprising at least one secondary separation means, such as a filter or packed column, in line with the fluid communication between the whole blood bag and/or blood component bags, thereby providing filtering of the whole blood and/or blood components as the whole blood and/or blood components flow from one bag to another.

16. The device of claim 1 or 15, wherein a micro-digital RF tag is affixed to the whole blood bag and the blood component bags, wherein the micro-digital RF tag contains manufacturing data such as lot codes of the bag set and the secondary separation means, and wherein information can be added to the tag such as the donor ID number, red blood cell bag ID number, platelet concentrate bag ID number, plasma bag ID number, operator number, purity of platelet concentrate, the time of collection of the whole blood, temperature profile and speed profile.

17. The device of claim 16, wherein data is read from the RF ID tag and data can be added to the RF ID tag, wherein the data is used to set processing control parameters such as temperature, time, g-force and valve timing and wherein the actual output of the processing control parameters are recorded.

18. The device of claim 16, wherein the data is automatically added to the tag as the cassette is placed in the centrifuge.

19. The device of claim 15, wherein the at least one secondary separation means is positioned in between the whole blood bag and a platelet concentrate bag and wherein platelet rich plasma supernatant is expressed through the secondary separation device as the platelet rich plasma supernatant flows from the whole blood bag to the platelet concentrate bag.

20. The device of claim 19, wherein the at least one secondary separation means is a leukodepleting filter.

21. The device of claim 15, wherein the at least one secondary separation means is a separation means that is operated statically at zero rpm to prevent the centrifugal force from interfering with the separation capacity of the separation means.

22. The device of claim 21, further including a holding bag between the whole blood bag and a platelet concentrate bag, wherein after the centrifuge spins the one or more cassettes, and the whole blood in the whole blood bag separates into its components, platelet rich plasma from the whole blood bag is expressed into the holding bag and after the centrifugal speed is zero, the platelet rich plasma in the holding bag is expressed through the at least one secondary separation means and into the platelet concentrate bag.

23. The device of claim 1, further comprising a first optical sensor situated to monitor the fluid flow between the whole blood bag and a platelet concentrate bag and a plasma bag.

24. The device of claim 23, further comprising a first valve positioned in the fluid flow between the whole blood bag and the platelet concentrate bag and plasma bag, wherein when the first optical sensor detects the presence of red blood cells in the fluid flow between the whole blood bag and a platelet concentrate bag and a plasma bag, the first valve closes off the fluid flow between the whole blood bag and the platelet concentrate bag and plasma bag.

25. The device of claim 24, further comprising a second valve positioned between the fluid flow between the whole blood bag and a red blood cell bag, wherein when the first valve closes off the fluid flow between the whole blood bag and the platelet concentrate bag and plasma bag, the second valve opens up the fluid flow between the whole blood bag and red blood cell bag.

26. The device of claim 25, further comprising a third valve positioned in the fluid flow between the platelet concentrate bag and plasma bag and a fourth valve positioned between the platelet concentrate bag and the whole blood bag, wherein the valves prevent the remixing of components within the different blood component bags during the rapid deceleration of the centrifuge.

27. The device of claim 23, wherein the valve is a single 3-way valve that is further positioned between the fluid flow between the whole blood bag and a red blood cell bag and wherein after the 3-way valve closes off the fluid flow between the whole blood bag and the platelet concentrate bag and plasma bag, the single 3-way valve then opens up the fluid flow between the whole blood bag and red blood cell bag.

28. The device of claim 23, wherein the optical sensor monitors the conditions of the fluid flow for measuring whether the materials flowing from one bag to another bag are within acceptable limits.

29. The device of claim 1, further including an optical sensing means for optically identifying manufacturing information, such as lot code and part number from the bags that are housed within the cassette as the cassette is placed in the centrifuge.

30. The device of claim 29, wherein the optical sensing means is a bar code reader.

31. A method for separating blood into its components comprising utilizing the device of any one of claims 1–21 and 29–22.

32. A method for the separation of whole blood into its components, the method comprising the steps of:
collecting a unit of whole blood in at least one whole blood bag;
providing a centrifuge device and a plurality of cassettes structured and constructed to be placed in the centrifuge, each cassette having a plurality of sections including an expressor chamber or expressor bag section, wherein the plurality of cassettes are stacked in a co-axial configuration in the centrifuge;
placing at least one whole blood bag into a section in a cassette;
placing at least one cassette holding the whole blood bag into the centrifuge;
causing the centrifuge to spin;
allowing the whole blood to separate into its components;
introducing expressor fluid or gas to the expressor chamber or expressor bag; and
allowing the expressor fluid or gas to force the blood components to flow into separate collection bags.

33. A method for the separation of whole blood into its components, the method comprising the steps of:
(a) providing an automated device for separating blood into its components comprising:
one or more cassettes;
a plurality of cavities in each cassette for housing at least a whole blood bag and at least one blood component bag;
the whole blood bag and blood component bags in fluid communication with each other;
(b) placing a whole blood bag holding whole blood and at least one blood component bag in the plurality of cavities in each cassette;
(c) placing the one or more cassettes into a centrifuge;
(d) spinning the centrifuge;
(e) allowing the red blood cells to separate from the plasma in the whole blood bag;
(f) allowing the plasma to flow from the whole blood bag to a first blood component bag;
(g) allowing the platelets to sediment radially and collect on the surfaces of the first blood component bag; and
(h) allowing the plasma minus the platelets collected on the surfaces of the first blood component bag to flow through the first blood component bag into a second blood component bag.

34. The method of claim 33, further comprising the steps of:
allowing the red blood cells in the whole blood bag to flow from the whole blood bag to a third blood component bag.

35. The method of claim 33, wherein each cassette further comprises an expressor bag or expressor chamber sealed by a flexible membrane in contact with the whole blood bag and/or at least one blood component bag, and wherein the method further comprises the steps of:
after allowing the red blood cells to separate from the plasma in the whole blood bag; feeding expressor fluid or gas into the expressor chamber or expressor bag such that the flexible membrane or expressor bag expands against the whole blood bag and/or at least one blood component bag; allowing the expressor bag or flexible membrane to compress the whole blood bag and/or at least one blood component bag to force separated blood components to flow into different blood component bags.

36. The method of claim 33, wherein the device further includes at least one filter in line with the fluid communication between the whole blood bag and/or blood component bags, thereby providing filtering of the whole blood and/or blood components as the whole blood and/or blood components flow from one bag to another.

37. The method of claim 33, wherein the device further comprises a first optical sensor situated to monitor the fluid flow between the whole blood bag and first blood component bag, and a first valve positioned in between the fluid flow between the whole blood bag and first blood component bag, and wherein the method further comprises the steps of:
monitoring the fluid flow of the plasma from the whole blood bag to the first blood component bag, for red blood cells; and
closing off the first valve when red blood cells are monitored.

38. The method of claim 37, wherein the device further comprises a second valve positioned between the whole blood bag and the third blood component bag and wherein the method further comprises the steps of:
opening the second valve after closing off the first valve, thereby allowing the red blood cells to flow into the third blood component bag.

39. The method of claim 37, further comprising:
using the first optical sensor to measure whether the materials flowing from the whole blood bag to the first blood component bag are within acceptable limits.

40. The method of claim 39, further comprising a third valve positioned in the fluid flow between the platelet concentrate bag and plasma bag and a fourth valve positioned between the platelet concentrate bag and the whole blood bag, wherein the valves prevent the remixing of components within the different blood component bags during the rapid deceleration of the centrifuge.

* * * * *